(12) United States Patent
Singh et al.

(10) Patent No.: US 6,214,358 B1
(45) Date of Patent: Apr. 10, 2001

(54) **PROTEIN ALLERGENS OF THE SPECIES *CYNODON DACTYLON***

(75) Inventors: Mohan Bir Singh, Templestowe; Penelope Smith, North Fitzroy; Robert Bruce Knox, North Balwyn, all of (AU)

(73) Assignee: ImmuLogic Pharamaceutical Corp., Waltham, MA (US)

( * ) Notice: Subject to any disclaimer, the term of this patent is extended or adjusted under 35 U.S.C. 154(b) by 0 days.

(21) Appl. No.: 08/441,507

(22) Filed: May 15, 1995

Related U.S. Application Data

(62) Division of application No. 07/969,875, filed on Oct. 30, 1992, now abandoned.

(51) Int. Cl.$^7$ .................................................. A61K 39/35
(52) U.S. Cl. .................................... 424/275.1; 424/184.1; 424/185.1; 424/192.1; 435/69.7; 435/252.3; 530/350; 530/370; 536/23.6
(58) Field of Search ............................. 424/184.1, 185.1, 424/275.1, 276.1, 192.1; 435/69.3, 172.3, 240.2, 320.1, 252.3; 536/23.1, 23.6, 24.1; 514/2; 530/350, 324–329, 370

(56) References Cited

U.S. PATENT DOCUMENTS 5,480,972 * 1/1996 Avjioglu et al. ..................... 530/379

FOREIGN PATENT DOCUMENTS

WO 8909260 10/1989 (WO) .

OTHER PUBLICATIONS

Perez et al., The Journal of Biological Chemistry, vol. 265, No. 27, pp. 16210–16215, 1990.*

Ford et al., J. Allergy Clin. Immunol., vol. 79, No. 5, pp. 711–720, May 1987.*

Matthiesen, et al., "Characterization of the major allergen of *Cynodon dactylon* . . . ", *J. Allergy Clin. Immunol.*, Nov. 1991, vol. 88, No. 5, pp. 765–774.

Matthiesen, et al., "Monoclonal Antibodies against group I and group V Allergens of Grass Pollens", Abstracts of EAACI 1990 meeting, OP48, p. 47.

Singh, et al., "Molecular Biology of Rye–Grass Pollen Allergens," Baldo BA (ed): Molecular Approaches to the Study of Allergens, Monogr. Allergy, Basel, Karger, 1990, vol. 28:101–120.

Matthiesen, et al., "Characteristics of grass pollen allergens," from Workshop held under Aegis of XIV Congress of European Academy of Allergy & Clin. Immunol., Berlin, Sep. 1989.

Chang, et al., "Analysis of allergenic components of Bermuda grass pollen by monoclonal antibodies", *Allergy*, 1991, vol. 46:520–528.

Matthiesen, et al., "Characterization of the major allergen of Cynodon Dectylon (Bermuda Grass) pollen", *J. Allergy Clin. Immun.*, 1988, vol. 81:266 (Abstract).

Tovey, et al., "Characterisation of allergens by protein blotting", *Electrophoresis*, 1987, vol. 8, pp 452–463.

* cited by examiner

*Primary Examiner*—Laurie Scheiner
(74) *Attorney, Agent, or Firm*—Lahive & Cockfield, LLP

(57) ABSTRACT

The present invention provides nucleic acid sequences coding Cyn d I, or at least one fragment thereof or the functional equivalent of such nucleic acid sequences. The present invention also provides expression vectors comprising such nucleic acid sequences and host cells transformed therewith. The present invention further provides isolated Bermuda grass pollen protein allergen Cyn d I or fragments thereof. Isolated Bermuda grass pollen protein allergens or antigenic or allergenic fragments thereof are useful for diagnosing and treating sensitivity in an individual to Bermuda grass pollen allergens.

3 Claims, 26 Drawing Sheets

```
          10        20        30        40        50        60
           |         |         |         |         |         |
C2 5'-CACATTGCTGCCTACCACTTCGACCTCTCCGGCAAAGCCTTCGGCGCCATGGCCAAGAAG
       H  I  A  A  Y  H  F  D  L  S  G  K  A  F  G  A  M  A  K  K 70        80        90       100       110       120
           |         |         |         |         |         |
     GGAGAGGAGGACAAGCTGCGCAAGGCCGGCGAACTGATGCTGCAGTTCCGCCGTGTCAAG
       G  E  E  D  K  L  R  K  A  G  E  L  M  L  Q  F  R  R  V  K 130       140       150       160       170       180
           |         |         |         |         |         |
     TGCGAGTACCCATCCGACACCAAGATCGCCTTCCACGTCGAGAAGGGCTCAAGCCCCAAT
       C  E  Y  P  S  D  T  K  I  A  F  H  V  E  K  G  S  S  P  N

L90       200       210       220       230       240
           |         |         |         |         |         |
     TACCTGGCGCTGCTCGTGAAGTACGCTGCCGGCGATGGCAACATTGTCGGTGTCGACATC
       Y  L  A  L  L  V  K  Y  A  A  G  D  G  N  I  V  G  V  D  I 250       260       270       280       290       300
           |         |         |         |         |         |
     AAGCCCAAGGGCTCCGACGAGTTCCTGCCCATGAAGCAGTCGTGGGGCGCCATCTGGAGG
       K  P  K  G  S  D  E  F  L  P  M  K  Q  S  W  G  A  I  W  R 310       320       330       340       350       360
           |         |         |         |         |         |
     ATCGACCCCCCCAAGCCACTTAAGGGTCCCTTCACCATCCGCCTCACCAGTGAGAGTGGC
       I  D  P  P  K  P  L  K  G  P  F  T  I  R  L  T  S  E  S  G 370       380       390       400       410       420
           |         |         |         |         |         |
     GGCCATGTCGAACAGGACGATGTCATCCCCGAAGACTGGAAGCCCGACACCGTCTACAAG
       G  H  V  E  Q  D  D  V  I  P  E  D  W  K  P  D  T  V  Y  K 430       440       450       460       470       480
           |         |         |         |         |         |
     TCCAAGATCCAGTTCTGAGCATTGATGTGCCCGGAATTATCGTCCACGCGATATAACCCA
       S  K  I  Q  F  -

490       500       510       520       530       540
           |         |         |         |         |         |
     GCCATGAGTTTGTGGTATCTTTTTACTTTTCTTATTCTTTTTTGCAAGAAAGGGTTTACG 550       560       570       580       590       600
           |         |         |         |         |         |
     GAATATGCATGCATGCCATATCTAACAAGCATGCATGCTTTTCTCTCCTTTTTTTCTACT 610       620       630       640       650       660
           |         |         |         |         |         |
     ATTATTGCATCTCCACAATTCCATGTGGAGAGTTTTGATGAACAACAAGGTATACTCGTG
CC-3'
```

Fig. 1

```
                  10         20         30         40         50         60
                   |          |          |          |          |          |
C18 5'-GTCGACAAGCCTCCCTTCGACGGCATGACCGCCTGCGGCAACGAGCCCATCTTCAAGGAC
        V  D  K  P  P  F  D  G  M  T  A  C  G  N  E  P  I  F  K  D 70         80         90        100        110        120
                   |          |          |          |          |          |
       GGCCTCGGCTGCGGCGCATGCTACGAGATCAAGTGCAAGGAACCCGTCGAGTGCTCCGGC
        G  L  G  C  G  A  C  Y  E  I  K  C  K  E  P  V  E  C  S  G 130        140        150        160        170        180
                   |          |          |          |          |          |
       GAGCCCGTCCTCGTCAAGATCACCGACAAGAACTACGAGCACATCGCCGCCTACCACTTC
        E  P  V  L  V  K  I  T  D  K  N  Y  E  H  I  A  A  Y  H  F 190        200        210        220        230        240
                   |          |          |          |          |          |
       GACCTCTCCGGCAAGGCCTTCGGCGCCATGGCCAAGAAGGGCCAGGAAGACAAGCTGCGC
        D  L  S  G  K  A  F  G  A  M  A  K  K  G  Q  E  D  K  L  R 250        260        270        280        290        300
                   |          |          |          |          |          |
       AAGGCCGGTGAGCTGACTCTGCAGTTCCGCCGCGTCAAGTGCAAGTACCCCTCCGGCACC
        K  A  G  E  L  T  L  Q  F  R  R  V  K  C  K  Y  P  S  G  T 310        320        330        340        350        360
                   |          |          |          |          |          |
       AAGATCACCTTCCACATCGAGAAGGGATCCAACGACCATTACCTGGCGCTGCTCGTCAAG
        K  I  T  F  H  I  E  K  G  S  N  D  H  Y  L  A  L  L  V  K 370        380        390        400        410        420
                   |          |          |          |          |          |
       TACGCCGCCGGCGATGGCAACATTGTCGCCGTCGACATCAAGCCCAAGGACTCCGACGAG
        Y  A  A  G  D  G  N  I  V  A  V  D  I  K  P  K  D  S  D  E 430        440        450        460        470        480
                   |          |          |          |          |          |
       TTCATTCCCATGAAGTCGTCCTGGGGCGCCATCTGGAGGATCGACCCCAAGAAGCCGCTC
        F  I  P  M  K  S  S  W  G  A  I  W  R  I  D  P  K  K  P  L 490        500        510        520        530        540
                   |          |          |          |          |          |
       AAGGGCCCCTTCTCCATCCGCCTCACCTCCGAGGGCGGCGCCCATCTCGTCCAGGACGAC
        K  G  P  F  S  I  R  L  T  S  E  G  G  A  H  L  V  Q  D  D 550        560        570        580        590        600
                   |          |          |          |          |          |
       GTCATCCCAGCCAACTGGAAGCCAGACACCGTCTACACCTCCAAGCTCCAGTTCGGAGCC
        V  I  P  A  N  W  K  P  D  T  V  Y  T  S  K  L  Q  F  G  A
```

Fig. 2

```
          610       620       630       640       650       660
           |         |         |         |         |         |
TGAGAGACGATGATCCTCCATGCATATCCTCGCCGATTGCAAGGGCTCATATATGACATG 670       680       690       700       710       720
           |         |         |         |         |         |
TGCGTGTACGCATCTGTCGAATAAGCATCCATATATGCATGAGTTTAATATTTCTTTTTA 730       740       750       760       770
           |         |         |         |         |
TTTCCCCCCTTCAATTATATGTACATCTCAATGTGGAGAGTTATTTTCTCGTGCC-3'
```

Fig. 2 (Continued)

The character to show that two aligned residues are identical is '|'

```
C18  5' GTCGACAAGCCTCCCTTCGACGGCATGACCGCCTGCGGCAACGAGCCCAT  -50

C18     CTTCAAGGACGGCCTCGGCTGCGGCGCATGCTACGAGATCAAGTGCAAGG  -100
        ------------------------
C18     AACCCGTCGAGTGCTCCGGCGAGCCCGTCCTCGTCAAGATCACCGACAAG  -150

C18     AACTACGAGCACATCGCCGCCTACCACTTCGACCTCTCCGGCAAGGCCTT  -200
                 | |||||||||||||||||||||||||| |||||
C2      ---------CACATTGCTGCCTACCACTTCGACCTCTCCGGCAAAGCCTT  -41

C18     CGGCGCCATGGCCAAGAAGGGCCAGGAAGACAAGCTGCGCAAGGCCGGTG  -250
        |||||||||||||||||||||| |||  ||||||||||||||||||||| |
C2      CGGCGCCATGGCCAAGAAGGGAGAGGAGGACAAGCTGCGCAAGGCCGGCG  -91

C18     AGCTGACTCTGCAGTTCCGCCGCGTCAAGTGCAAGTACCCCTCCGGCACC  -300
        | |||| ||||||||||||||| ||||||||||| ||||| ||| ||||
C2      AACTGATGCTGCAGTTCCGCCGTGTCAAGTGCGAGTACCCATCCGACACC  -141

C18     AAGATCACCTTCCACATCGAGAAGGGATCCAACGACCATTACCTGGCGCT  -350
        ||||| || |||||| |||||||||| ||| ||| |||||||||||||
C2      AAGATCGCCTTCCACGTCGAGAAGGGCTCAAGCCCCAATTACCTGGCGCT  -191

C18     GCTCGTCAAGTACGCCGCCGGCGATGGCAACATTGTCGCCGTCGACATCA  -400
        ||||||| |||||||| ||||||||||||||||||||| || |||||||
C2      GCTCGTGAAGTACGCTGCCGGCGATGGCAACATTGTCGGTGTCGACATCA  -241

C18     AGCCCAAGGACTCCGACGAGTTCATTCCCATGAAGTCGTCCTGGGGCGCC  -450
        |||||||| |||||||||||||| |||||||||||| |||| |||||||
C2      AGCCCAAGGGCTCCGACGAGTTCCTGCCCATGAAGCAGTCGTGGGGCGCC  -291

C18     ATCTGGAGGATCGACCCCAAGAAGCCGCTCAAGGGCCCCTTCTCCATCCG  -500
        ||||||||||||||||||  |||||| || |||||| |||||||||||||
C2      ATCTGGAGGATCGACCCCCCCAAGCCACTTAAGGGTCCCTTCACCATCCG  -341

C18     CCTCACCTCCGAGGGCGGCGCCCATCTCGTCCAGGACGACGTCATCCCAG  -550
        |||||| || |  || |||||||||  || ||||||||||||||||||| 
C2      CCTCACCAGTGAGAGTGGCGGCCATGTCGAACAGGACGATGTCATCCCCG  -391

C18     CCAACTGGAAGCCAGACACCGTCTACACCTCCAAGCTCCAGTTCGGAGCC  -600
          | |||||||||  ||||||||||||| || || |||| |||||  || 
C2      AAGACTGGAAGCCCGACACCGTCTACAAGTCCAAGATCCAGTTCTGAGCA  -441

C18     T-GA-GAGAC-G--ATGATCCTCCATGC-ATAT--CCTCGCC---GATTGC  -640
        | || |  || |  |||||  ||||||| |||| |||| ||   |||| 
C2      TTGATGTGCCCGGAATTATCGTCCACGCGATATAACCCAGCCATGAGTTT  -491

C18     AAGGGCTCATAT-A--TGACATGTGCGTGTACGCATCT----GT---CG-  -679
         || ||| ||||    |  ||  |  || |||  |||    ||   ||
C2      GTGGTATCTTTTTACTTTTCTTATTCTTTTTTGCAAGAAAGGGTTTACGG  -541

C18     AATAAGCATCCAT---ATATGCATGA-GTTTA-ATA--TTTCTTTT-TAT  -721
        |||| |||||||    ||||||||| |  |  ||   |||||||| |||
C2      AATATGCATGCATGCCATATCTAACAAGCATGCATGCTTTTCTCTCCTTT  -591
```

Fig. 3

```
C18    TTCCCCCCTTCAATTATATGT--ACATCTCAATGTGGAGAGTT---AT-- -764
       || | || ||| ||| ||| || |||||||||||  ||
C2     TTTTCTACTATTATTGCATCTCCACAATTCCATGTGGAGAGTTTTGATGA -641

C18    ---------TTT-CTCGTGCC -775 - 3'
                || |||||||||
C2     ACAACAAGGTATACTCGTGCC -662
```

Fig. 3 (Continued)

```
C18 - VDKPPFDGMTACGNEPIFKDGLGCGACYEIKCKEPVECSGEPVLVKITDK      -50

C18 - NYEHIAAYHFDLSGKAFGAMAKKGQEDKLRKAGELTLQFRRVKCKYPSGT     -100
         ||||||||||||||||||||||| ||||||||| |||||||| ||| |
C2  -    HIAAYHFDLSGKAFGAMAKKGEEDKLRKAGELMLQFRRVKCEYPSDT      -47

C18 - KITFHIEKGSNDHYLALLVKYAAGDGNIVAVDIKPKDSEFIPMKSSWGA     -150
       ||s||s||||   |||||||||||||| |||||| ||||s||| ||||
C2  - KIAFHVEKGSSPNYLALLVKYAAGDGNIVGVDIKPKGSDEFLPMKQSWGA      -97

C18 - IWRIDPKKPLKGPFSIRLTSEGGAHLVQDDVIPANWKPDTVYTSKLQFGA     -200
       |||||| ||||||s|||||| | |s |||||| |||||||| ||s||
C2  - IWRIDPPKPLKGPFTIRLTSESGGHVEQDDVIPEDWKPDTVYKSKIQF       -145
```

Fig. 4

```
           50         60         70         80         90        100
            |          |          |          |          |          |
C18   VDKPPFDGMTACGNEPIFKDGLGCGACYEIKCKEPVECSGEPVLVKITDKNYEH
C22   ------------------------------------------------------
C23   ------------------------------------------------------
C2    ------------------------------------------------------

110        120        130        140        150        160
            |          |          |          |          |          |
C18   IAAYHFDLSGKAFGAMAKKGQEDKLRKAGELTLQFRRVKCKYPSGTKITFHIEKGSNDHY
C22   ---------------------------------------------------------
C23   ---------------------------------------------------------
C2    --------------------E---------M--------E---D---A--V----SPN-
C3    --------------------E---------M--------E---D---A--v-----PN- 170        180        190        200        210        220
            |          |          |          |          |          |
C18   LALLVKYAAGDGNIVAVDIKPKDSDEFIPMKSSWGAIWRIDPKKPLKGPFSIRLTSEGGA
C21   ---------------------------------------------------------
C33              --------------------------------------------
C22   ---------------------------------------------------------
C23   ---------------------------------------------------------
C2    ---------------G------G----L---Q----------P-------T------S-G
C3    ---------------S----S-G--D-L---Q----------P-------T------S-G 230        240
            |          |
C18   HLVQDDVIPANWKPDTVYTSKLQFGA
C21   -------------------------
C33   -------------------------
C22   -------------------------
C23   -------------------------
C2    -VE-------ED-------K--I--
C3    -VE-E----ED-------K--I--
```

```
         10        20        30        40        50
         |         |         |         |         |
5'-ATTGATCATTGGAATCCATTACATACAGAAGCAGCAAGAAATGGCGCACA
                                              M  A  H 60        70        80        90       100
         |         |         |         |         |
   CGAAACTGGCGCTGGTTGCGGTGCTTGTGGCTGCGATGGTGGCCGGGCGG
    T  K  L  A  L  V  A  V  L  V  A  A  M  V  A  G  R 100       120       130       140       150
         |         |         |         |         |
   GTCGTGGCCATCGGCGACAAGCCAGGGCCCAACATCACGGCGACCTACGG
    V  V  A  I  G  D  K  P  G  P  N  I  T  A  T  Y  G 160       170       180       190       200
         |         |         |         |         |
   CAACAAGTGGCTGGAGGCCAAGGCCACTTTCTACGGTAGCAACCCACGCG
    N  K  W  L  E  A  K  A  T  F  Y  G  S  N  P  R 210       220       230       240       250
         |         |         |         |         |
   GTGCCGCCCCCGATGACCACGGCGGCGCTTGCGGGTACAAGGACGTCGAC
    G  A  A  P  D  D  H  G  G  A  C  G  Y  K  D  V  D

260
         |
   AAGCCTCCCTTCG -3'
    K  P  P  F
```

```
           10         20         30         40         50         60
            |          |          |          |          |          |
5'- GTCCGATCGATCATTCACAAGCAAGAAATGGCGCAGACCACGATGAATCAGAAACTGGCG
                                  M  A  Q  T  T  M  N  Q  K  L  A 70         80         90        100        110        120
            |          |          |          |          |          |
    CTGGTTGCGTGGCCCGTGGCTGCGATGGTGGCCGGGCGGGTCGTGGCCATCGGCGACAAG
     L  V  A  W  P  V  A  A  M  V  A  G  R  V  V  A  I  G  D  K 130        140        150        160        170        180
            |          |          |          |          |          |
    CCAGGGCCCAACATCACAGCGACCTACGGCAGCAAGTGGCTGGAGGCCAAGGCCACCTTC
     P  G  P  N  I  T  A  T  Y  G  S  K  W  L  E  A  K  A  T  F 190        200        210        220        230        240
            |          |          |          |          |          |
    TACGGCAGCAACCCGCGCGGTGCCGCCCCCGATGACCACGGCGGCGCTTGCGGGTACAAG
     Y  G  S  N  P  R  G  A  A  P  D  D  H  G  G  A  C  G  Y  K 250        260
            |          |
    GACGTCGACAAGCCTCCCTTCG- 3'
     D  V  D  K  P  P  F
```

Fig. 7

Cyn d I.14

```
        -20           -10            1         10         20         30
         |             |             |          |          |          |
     Q TMNQ         WP                                   G
   MA H T****KLALVA VL VAAMVAGRVVAIGDKPGPNITATYG N KWLEAKATFYGSNP 40            50
         |             |
                    KD
   RGAAPDDHGGACGY RN VDKPPF
```

Fig. 8

Cyn d I.18

```
        -20            -10             1             10            20            30
         |              |              |              |             |             |
      Q  TMNQ          WP
   MA H T****  KLALVA  VL  VAAMVAGRVVAIGDKPGPNITATYG G  KWLEAKATFYGSNP
                                                     N 40             50             60             70            80            90
         |              |              |              |             |             |
                         KD
   RGAAPDDHGGACGY RN  VDKPPFDGMTACGNEPIFKDGLCGCACYEIKCKEPVECSGEPVL 100            110            120            130           140           150
         |              |              |              |             |             |
   VKITDKNYEHIAAYHFDLSGKAFGAMAKKGQEDKLRKAGELTLQFRRVKCKYPSGTKITF 160            170            180            190           200           210
         |              |              |              |             |             |
   HIEKGSNDHYLALLVKYAAGDGNIVAVDIKPKDSDEFIPMKSSWGAIWRIDPKKPLKGPF 220            230            240
         |              |              |
   SIRLTSEGGAHLVQDDVIPANWKPDTVYTSKLQFGA
```

Fig. 9

Cyn d I.2/3

```
          100       110       120       130       140       150
           |         |         |         |         |         |
            HIAAYHFDLSGKAFGAMAKKGEEDKLRKAGELMLQFRRVKCEYPSDTKIAF 160       170       180       190       200       210
           |         |         |         |         |         |
                    S                G       P          E
          HVEKGS PNYLALLVKYAAGDGNIV VDIK KGSD FLPMKQSWGAIWRIDPPKPLKGPF
                    N                S       S          D 220       230       240
           |         |         |
                        D
          TIRLTSESGGHVEQ DVIPEDWKPDTVYKSKIQF
                        E
```

Fig. 10

| 1 | 2 | 3 | 4 | 5 | 6 | 7 | 8 | 13 | 15 |
|---|---|---|---|---|---|---|---|----|----|
| 16 | 18 | 19 | 20 | 21 | 22 | 23 | 24 | 25 | 26 |
| 27 | 28 | 29 | 31 | 32 | 33 | 34 | 35 | 36 | 37 |
| 1 | 1 | | | | | | | | |

| 1 | 2 | 3 | 4 | 5 | 6 | 7 | 8 | 13 | 15 |
|---|---|---|---|---|---|---|---|----|----|
| 16 | 18 | 19 | 20 | 21 | 22 | 23 | 24 | 25 | 26 |
| 27 | 28 | 29 | 31 | 32 | 33 | 34 | 35 | 36 | 37 |
| 1 | 1 | | | | | | | | |

```
       10         20         30         40         50         60
        |          |          |          |          |          |
C3 5'-GACCTTTCTGGCAAGGCGTTCGGCGCCATGGCCAAGAAGGGCGAGGAGGACAAGCTGCGC
      D  L  S  G  K  A  F  G  A  M  A  K  K  G  E  E  D  K  L  R 70         80         90        100        110        120
        |          |          |          |          |          |
    AAGGCCGGCGAGCTGATGCTGCAGTTCCGCCGCGTCAAGTGCGAGTACCCATCCGACACC
      K  A  G  E  L  M  L  Q  F  R  R  V  K  C  E  Y  P  S  D  T 130        140        150        160        170        180
        |          |          |          |          |          |
    AAGATCGCCTTCCACGTTGAGAAGGGCTCCAACCCCAATTACCTGGCGCTGCTCGTGAAG
      K  I  A  F  H  V  E  K  G  S  N  P  N  Y  L  A  L  L  V  K 190        200        210        220        230        240
        |          |          |          |          |          |
    TACGCGGCCGGCGACGGCAATATCGTCAGTGTCGATATCAAGTCCAAGGGCTCCGACGAC
      Y  A  A  G  D  G  N  I  V  S  V  D  I  K  S  K  G  S  D  D 250        260        270        280        290        300
        |          |          |          |          |          |
    TTCCTGCCCATGAAGCAGTCGTGGGGCGCCATCTGGAGGATCGATCCCCCCAAGCCGCTC
      F  L  P  M  K  Q  S  W  G  A  I  W  R  I  D  P  P  K  P  L 310        320        330        340        350        360
        |          |          |          |          |          |
    AAGGGTCCCTTCACGATCCGCCTCACCAGCGAGAGTGGCGGCCATGTCGAACAGGAAGAT
      K  G  P  F  T  I  R  L  T  S  E  S  G  G  H  V  E  Q  E  D 370        380        390        400        410        420
        |          |          |          |          |          |
    GTCATCCCCGAAGACTGGAAGCCCGACACCGTCTACAAGTCCAAGATCCAGTTCTGAGCC
      V  I  P  E  D  W  K  P  D  T  V  Y  K  S  K  I  Q  F  -

430        440        450        460        470        480
        |          |          |          |          |          |
    TGATGTGCCCACAAACAGCGTGCACACTAATAACACAACCTTATGACATCTTTGTTTCTT 490        500        510        520        530        540
        |          |          |          |          |          |
    TTTTGCAAGAAACAGTCTATGCGATCTGCATGCATGCATACATATAATAACAAGTATCGA 550        560        570        580        590
        |          |          |          |          |
    TGCGCGCGTGAGGTTTTTCTCTCCTTTTCTTTCTACTATTATTGTTGCATTTCC  -  3'
```

Fig. 15

```
             10        20        30        40        50        60
              |         |         |         |         |         |
C22 5'- GACAAGCCTCCCTTCGACGGCATGACCGCCTGCGGCAACGAGCCCATCTTCAAGGACGGC
         D  K  P  P  F  D  G  M  T  A  C  G  N  E  P  I  F  K  D  G 70        80        90       100       110       120
              |         |         |         |         |         |
        CTCGGCTGCGGCGCATGCTACGAGATCAAGTGCAAGGAACCCGTCGAGTGCTCCGGCGAG
         L  G  C  G  A  C  Y  E  I  K  C  K  E  P  V  E  C  S  G  E 130       140       150       160       170       180
              |         |         |         |         |         |
        CCCGTCCTCGTCAAGATCACCGACAAGAACTACGAGCACATCGCCGCCTACCACTTCGAC
         P  V  L  V  K  I  T  D  K  N  Y  E  H  I  A  A  Y  H  F  D 190       200       210       220       230       240
              |         |         |         |         |         |
        CTCTCCGGCAAGGCCTTCGGCGCCATGGCCAAGAAGGGCCAGGAAGACAAGCTGCGCAAG
         L  S  G  K  A  F  G  A  M  A  K  K  G  Q  E  D  K  L  R  K 250       260       270       280       290       300
              |         |         |         |         |         |
        GCCGGTGAGCTGACTCTGCAGTTCCGCCGCGTCAAGTGCAAGTACCCCTCCGGCACCAAG
         A  G  E  L  T  L  Q  F  R  R  V  K  C  K  Y  P  S  G  T  K 310       320       330       340       350       360
              |         |         |         |         |         |
        ATCACCTTCCACATCGAGAAGGGATCCAACGACCATTACCTGGCGCTGCTCGTCAAGTAC
         I  T  F  H  I  E  K  G  S  N  D  H  Y  L  A  L  L  V  K  Y 370       380       390       400       410       420
              |         |         |         |         |         |
        GCGGCCGGCGATGGCAACATTGTTGCTGTCGACATCAAGCCCAAGGACTCCGACGAGTTC
         A  A  G  D  G  N  I  V  A  V  D  I  K  P  K  D  S  D  E  F 430       440       450       460       470       480
              |         |         |         |         |         |
        ATTCCCATGAAGTCGTCCTGGGGCGCCATCTGGAGGATCGACCCCAAGAAGCCGCTCAAG
         I  P  M  K  S  S  W  G  A  I  W  R  I  D  P  K  K  P  L  K 490       500       510       520       530       540
              |         |         |         |         |         |
        GGCCCCTTCTCCATCCGCCTCACCTCCGAGGGCGGCGCCCATCTCGTCCAAGACGACGTC
         G  P  F  S  I  R  L  T  S  E  G  G  A  H  L  V  Q  D  D  V 550       560       570       580       590       600
              |         |         |         |         |         |
        ATCCCAGCCAACTGGAAGCCAGACACCGTCTACACCTCCAAGCTCCAGTTCTAAACACGC
         I  P  A  N  W  K  P  D  T  V  Y  T  S  K  L  Q  F  -
```

Fig. 16

```
          610       620       630       640       650       660
           |         |         |         |         |         |
AAAGGCTTATATTTGGAGCATATGAAGAATGCACACAAGCATGTGCTTCAGCTTCTCTTT 670       680       690       700       710       720
           |         |         |         |         |         |
TCTTTACTTTCCTTCATTGCATTGCATCTCATCATCTCCATATGTTTTTTAGATTTTGTG 730       740       750       760       770       780
           |         |         |         |         |         |
ATGCAAAGTGTCATAAGTGCCAAGGATTCAGGAGGCGCTTTAAGCAGTGTCGAGGATGTA 790       800
           |         |
GGGATCTCGTGCCGCTCGTGCC -3'
```

Fig. 16 (Continued)

```
           10         20         30         40         50         60
            |          |          |          |          |          |
C23 5'-CGACAAGCCTCCCTTCGACGGCATGACCGCCTGCGGCAACGAGCCCATCTTCAAGGACGG
        D  K  P  P  F  D  G  M  T  A  C  G  N  E  P  I  F  K  D  G 70         80         90        100        110        120
            |          |          |          |          |          |
     CCTCGGCTGCGGCGCATGCTACGAGATCAAGTGCAAGGAACCCGTCGAGTGCTCCGGCGA
      L  G  C  G  A  C  Y  E  I  K  C  K  E  P  V  E  C  S  G  E 130        140        150        160        170        180
            |          |          |          |          |          |
     GCCCGTCCTCGTCAAGATCACCGACAAGAACTACGAGCACATCGCCGCCTACCACTTCGA
      P  V  L  V  K  I  T  D  K  N  Y  E  H  I  A  A  Y  H  F  D 190        200        210        220        230        240
            |          |          |          |          |          |
     CCTCTCCGGCAAGGCCTTCGGCGCCATGGCCAAGAAGGGCCAGGAAGACAAGCTGCGCAA
      L  S  G  K  A  F  G  A  M  A  K  K  G  Q  E  D  K  L  R  K 250        260        270        280        290        300
            |          |          |          |          |          |
     GGCCGGTGAGCTGACTCTGCAGTTCCGCCGCGTCAAGTGCAAGTACCCCTCCGGCACCAA
      A  G  E  L  T  L  Q  F  R  R  V  K  C  K  Y  P  S  G  T  K 310        320        330        340        350        360
            |          |          |          |          |          |
     GATCACCTTCCACATCGAGAAGGGATCCAACGACCATTACCTGGCGCTGCTCGTCAAGTA
      I  T  F  H  I  E  K  G  S  N  D  H  Y  L  A  L  L  V  K  Y 370        380        390        400        410        420
            |          |          |          |          |          |
     CGCCGCCGGCGATGGCAACATTGTCGCCGTCGACATCAAGCCCAAGGACTCCGACGAGTT
      A  A  G  D  G  N  I  V  A  V  D  I  K  P  K  D  S  D  E  F 430        440        450        460        470        480
            |          |          |          |          |          |
     CATTCCCATGAAGTCGTCCTGGGGCGCCATCTGGAGGATCGACCCCAAGAAGCCGCTCAA
      I  P  M  K  S  S  W  G  A  I  W  R  I  D  P  K  K  P  L  K 490        500        510        520        530        540
            |          |          |          |          |          |
     GGGCCCCTTCTCCATCCGCCTCACCTCCGAGGGCGGCGCCCATCTCGTCCAGGACGACGT
      G  P  F  S  I  R  L  T  S  E  G  G  A  H  L  V  Q  D  D  V 550        560        570        580        590        600
            |          |          |          |          |          |
     CATCCCAGCCAACTGGAAGCCAGACACCGTCTACACCTCCAAGCTCCAGTTCTAAACACG
      I  P  A  N  W  K  P  D  T  V  Y  T  S  K  L  Q  F  -
```

Fig. 17

```
         610       620       630       640       650       660
          |         |         |         |         |         |
CAAAGGCTTATATTTGGAGCATATGAAGAATGCTCTCAAGCATGTGCTTCAGGAGTGCCC
         670       680       690       700       710       720
          |         |         |         |         |         |
ACGATGTAGGGATAACCGATTCATCAAAGCACATCATGTGAAACATCAGTTGAAAAAACT
         730       740       750       760       770       780
          |         |         |         |         |         |
GGTTGATTTTTTTATTATTATCGTGTAGATTTGGATGCTTTTGAAATCTTTTGTATTCTT
         790       800       810       820       830
          |         |         |         |         |
CATTGAGTTTACAAAATTACGCAATTGATGAGAGATGCCCTCTTGCATTTTT -3'
```

Fig. 17 (Continued)

Clone CDI

```
           10        20        30        40        50        60
           |         |         |         |         |         |
5'-GCCATCGGCGACAAGCCAGGGCCCAACATCACGGCGACCTACGGCAGCAAGTGGCTGGAG
    A  I  G  D  K  P  G  P  N  I  T  A  T  Y  G  S  K  W  L  E 70        80        90       100       110       120
           |         |         |         |         |         |
   GCCAGGGCCACCTTCTACGGCAGCAACCCGCGCGGTGCCGCCCCCGATGACCACGGCGGC
    A  R  A  T  F  Y  G  S  N  P  R  G  A  A  P  D  D  H  G  G 130       140       150       160       170       180
           |         |         |         |         |         |
   GCTTGCGGGTACAAGGACGTCGACAAGCCTCCCTTCGACGGCATGACCGCCTGCGGCAAC
    A  C  G  Y  K  D  V  D  K  P  P  F  D  G  M  T  A  C  G  N 190       200       210       220       230       240
           |         |         |         |         |         |
   GAGCCCATCTTCAAGGACGGCCTCGGCTGCGGCGCATGCTACGAGATCAAGTGCAAGGAA
    E  P  I  F  K  D  G  L  G  C  G  A  C  Y  E  I  K  C  K  E 250       260       270       280       290       300
           |         |         |         |         |         |
   CCCGTCGAGTGCTCCGGCGAGCCCGTCCTCGTCAAGATCACCGACAAGAACTACGAGCAC
    P  V  E  C  S  G  E  P  V  L  V  K  I  T  D  K  N  Y  E  H 310       320       330       340       350       360
           |         |         |         |         |         |
   ATCGCCGCCTACCACTTCGACCTCTCCGGCAAGGCCTTCGGCGCCATGGCCAAGAAGGGC
    I  A  A  Y  H  F  D  L  S  G  K  A  F  G  A  M  A  K  K  G 370       380       390       400       410       420
           |         |         |         |         |         |
   CAGGAAGACAAGCTGCGCAAGGCCGGTGAGCTGACTCTGCAGTTCCGCCGCGTCAAGTGC
    Q  E  D  K  L  R  K  A  G  E  L  T  L  Q  F  R  R  V  K  C 430       440       450       460       470       480
           |         |         |         |         |         |
   AAGTACCCCTCCGGCACCAAGATCACCTTCCACATCGAGAAGGGATCCAACGACCATTAC
    K  Y  P  S  G  T  K  I  T  F  H  I  E  K  G  S  N  D  H  Y 490       500       510       520       530       540
           |         |         |         |         |         |
   CTGGCGCTGCTCGTCAAGTACGCGGCCGGCGATGGCAACATTGTCGCCGTCGACATCAAG
    L  A  L  L  V  K  Y  A  A  G  D  G  N  I  V  A  V  D  I  K
```

Fig. 18

```
              550       560       570       580       590       600
               |         |         |         |         |         |
        CCCAGGGACTCCGACGAGTTCATTCCCATGAAGTCGTCCTGGGGCGCCATCTGGAGGATC
         P  R  D  S  D  E  F  I  P  M  K  S  S  W  G  A  I  W  R  I 610       620       630       640       650       660
               |         |         |         |         |         |
        GACCCCAAGAAGCCGCTCAAGGGCCCCTTCTCCATCCGCCTCACCTCCGAGGGCGGCGCC
         D  P  K  K  P  L  K  G  P  F  S  I  R  L  T  S  E  G  G  A 670       680       690       700       710       720
               |         |         |         |         |         |
        CATCTCGTCCAGGACGACGTCATCCCAGCCAACTGCAAGCCAGACACCGTCTACACCTCC
         H  L  V  Q  D  D  V  I  P  A  N  W  K  P  D  T  V  Y  T  S 730       740       750
               |         |         |
        AAGCTCCAGTTCGGAGCCTGAGAGACGATGATCCTCCAT-3'
         K  L  Q  F  G  A  -  E  T  M  I  L  H
```

Fig. 18 (Continued)

KAT-39-1

```
          10         20         30         40         50         60
           |          |          |          |          |          |
5'-CCAACATCACTGCAACCTACGGTGACAAGTGGCTGGATGCGAAGGCCACGTTCTACGGCA
    N  I  T  A  T  Y  G  D  K  W  L  D  A  K  A  T  F  Y  G 70         80         90        100        110        120
           |          |          |          |          |          |
   GCGACCCACGTGGCGCGGCCCCCGATGACCATGGCGGCGCGTGCGGATACAAGGACGTCG
    S  D  P  R  G  A  A  P  D  D  H  G  G  A  C  G  Y  K  D  V 130        140        150        160        170        180
           |          |          |          |          |          |
   ACAAGGCACCCTTCGACAGCATGACTGGATGCGGCAACGAGCCCATCTTCAAGGACGGTC
    D  K  A  P  F  D  S  M  T  G  C  G  N  E  P  I  F  K  D  G 190        200        210        220        230        240
           |          |          |          |          |          |
   TGGGCTGCGGCTCCTGCTACGAGATCAAGTGCAAGGAGCCAGCCGAGTGCTCAGGCGAGC
    L  G  C  G  S  C  Y  E  I  K  C  K  E  P  A  E  C  S  G  E 250        260        270        280        290        300
           |          |          |          |          |          |
   CCGTCCTCATTAAGATCACCGACAAGAACTACGAGCACATCGCCGCCTACCACTTCGACC
    P  V  L  I  K  I  T  D  K  N  Y  E  H  I  A  A  Y  H  F  D 310        320        330        340        350        360
           |          |          |          |          |          |
   TTTCTGGCAAGGCGTTCGGCGCCATGGCCAAGAAGGGCGAGGAGGACAAGCTGCGCAAGG
    L  S  G  K  A  F  G  A  M  A  K  K  G  E  E  D  K  L  R  K

CCGGCGAG-3'
    A  G  E
```

Fig. 19

```
              -20        -10         1         10        20        30
               |          |          |          |         |         |
                 Q  TMNQ      WP
Cyn d I.18   MA T**** KLALVA   VAAMVAGRVVAIGDKPGPNITATYG S KWLEAKATFYGSNP
                 H         VL                            N
Cyn d I.CD1                [-----]---------S-----R--------
Cyn d I.2/3 (full length)  [-(x)---]-------D---D--------D-

40         50        60         70        80        90
                |          |         |          |         |         |
Cyn d I.18   RGAAPDDHGGACGYKDVDKPPFDGMTACGNEPIFKDGLGCGACYEIKCKEPVECSGEPVL
Cyn d I.CD1  ------------------------------------------------------------
Cyn d I.2/3  ------------------A---S--G--------------S---------A--------
  (full length)

100        110       120        130       140       150
                |          |         |          |         |         |
Cyn d I.18   VKITDKNYEHIAAYHFDLSGKAFGAMAKKGQEDKLRKAGELTLQFRRVKCKYPSGTKITF
Cyn d I.CD1  ------------------------------------------------------------
Cyn d I.2/3  I-----------------------E----------M--------E---D---A-
  (full length)

160        170       180        190       200       210
                |          |         |          |         |         |
Cyn d I.18   HIEKGSNDHYLALLVKYAAGDGNIVAVDIKPKDSDEFIPMKSSWGAIWRIDPKKPLKGPF
Cyn d I.CD1  -----------------------------R------------------------------

Cyn d I.2/3  -V----S PN--------------G----P-G-E-L---Q-----------P-------
  (full length) N              S    S   D
```
```
               220        230       240
                |          |         |
Cyn d I.18   SIRLTSEGGAHLVQDDVIPANWKPDTVYTSKLQFGA
Cyn d I.CD1  -----------------------------------
Cyn d I.2/3  T------S-G-VE-D----ED-------K--I--
                          E
(full length)
```

Fig. 20

SEQUENCE LISTING (1) GENERAL INFORMATION:

(iii) NUMBER OF SEQUENCES: 52

(2) INFORMATION FOR SEQ ID NO: 1:

(i) SEQUENCE CHARACTERISTICS:
        (A) LENGTH: 662 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..435

(xi) SEQUENCE DESCRIPTION: SEQ ID NO: 1:

```
CAC ATT GCT GCC TAC CAC TTC GAC CTC TCC GGC AAA GCC TTC GGC GCC        48
His Ile Ala Ala Tyr His Phe Asp Leu Ser Gly Lys Ala Phe Gly Ala
 1               5                  10                  15

ATG GCC AAG AAG GGA GAG GAG GAC AAG CTG CGC AAG GCC GGC GAA CTG        96
Met Ala Lys Lys Gly Glu Glu Asp Lys Leu Arg Lys Ala Gly Glu Leu
            20                  25                  30

ATG CTG CAG TTC CGC CGT GTC AAG TGC GAG TAC CCA TCC GAC ACC AAG       144
Met Leu Gln Phe Arg Arg Val Lys Cys Glu Tyr Pro Ser Asp Thr Lys
        35                  40                  45

ATC GCC TTC CAC GTC GAG AAG GGC TCA AGC CCC AAT TAC CTG GCG CTG       192
Ile Ala Phe His Val Glu Lys Gly Ser Ser Pro Asn Tyr Leu Ala Leu
    50                  55                  60

CTC GTG AAG TAC GCT GCC GGC GAT GGC AAC ATT GTC GGT GTC GAC ATC       240
Leu Val Lys Tyr Ala Ala Gly Asp Gly Asn Ile Val Gly Val Asp Ile
65                  70                  75                  80

AAG CCC AAG GGC TCC GAC GAG TTC CTG CCC ATG AAG CAG TCG TGG GGC       288
Lys Pro Lys Gly Ser Asp Glu Phe Leu Pro Met Lys Gln Ser Trp Gly
                85                  90                  95
```

```
GCC ATC TGG AGG ATC GAC CCC CCC AAG CCA CTT AAG GGT CCC TTC ACC    336
Ala Ile Trp Arg Ile Asp Pro Pro Lys Pro Leu Lys Gly Pro Phe Thr
            100                 105                 110

ATC CGC CTC ACC AGT GAG AGT GGC GGC CAT GTC GAA CAG GAC GAT GTC    384
Ile Arg Leu Thr Ser Glu Ser Gly Gly His Val Glu Gln Asp Asp Val
                115                 120                 125

ATC CCC GAA GAC TGG AAG CCC GAC ACC GTC TAC AAG TCC AAG ATC CAG    432
Ile Pro Glu Asp Trp Lys Pro Asp Thr Val Tyr Lys Ser Lys Ile Gln
        130                 135                 140

TTC TGAGCATTGA TGTGCCCGGA ATTATCGTCC ACGCGATATA ACCCAGCCAT         485
Phe
145

GAGTTTGTGG TATCTTTTTA CTTTTCTTAT TCTTTTTTGC AAGAAAGGGT TTACGGAATA   545

TGCATGCATG CCATATCTAA CAAGCATGCA TGCTTTTCTC TCCTTTTTTT CTACTATTAT   605

TGCATCTCCA CAATTCCATG TGGAGAGTTT TGATGAACAA CAAGGTATAC TCGTGCC      662

(2) INFORMATION FOR SEQ ID NO: 2:

(i) SEQUENCE CHARACTERISTICS:
        (A) LENGTH: 145 amino acids
        (B) TYPE: amino acid
        (D) TOPOLOGY: linear (ii) MOLECULE TYPE: protein (xi) SEQUENCE DESCRIPTION: SEQ ID NO: 2:

His Ile Ala Ala Tyr His Phe Asp Leu Ser Gly Lys Ala Phe Gly Ala
 1               5                  10                  15

Met Ala Lys Lys Gly Glu Glu Asp Lys Leu Arg Lys Ala Gly Glu Leu
            20                  25                  30

Met Leu Gln Phe Arg Arg Val Lys Cys Glu Tyr Pro Ser Asp Thr Lys
        35                  40                  45

Ile Ala Phe His Val Glu Lys Gly Ser Ser Pro Asn Tyr Leu Ala Leu
    50                  55                  60

Leu Val Lys Tyr Ala Ala Gly Asp Gly Asn Ile Val Gly Val Asp Ile
65                  70                  75                  80

Lys Pro Lys Gly Ser Asp Glu Phe Leu Pro Met Lys Gln Ser Trp Gly
                85                  90                  95

Ala Ile Trp Arg Ile Asp Pro Pro Lys Pro Leu Lys Gly Pro Phe Thr
            100                 105                 110

Ile Arg Leu Thr Ser Glu Ser Gly Gly His Val Glu Gln Asp Asp Val
        115                 120                 125

Ile Pro Glu Asp Trp Lys Pro Asp Thr Val Tyr Lys Ser Lys Ile Gln
    130                 135                 140

Phe
145

(2) INFORMATION FOR SEQ ID NO: 3:

(i) SEQUENCE CHARACTERISTICS:
        (A) LENGTH: 775 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..600
```

(xi) SEQUENCE DESCRIPTION: SEQ ID NO: 3:

```
GTC GAC AAG CCT CCC TTC GAC GGC ATG ACC GCC TGC GGC AAC GAG CCC        48
Val Asp Lys Pro Pro Phe Asp Gly Met Thr Ala Cys Gly Asn Glu Pro
 1               5                  10                  15

ATC TTC AAG GAC GGC CTC GGC TGC GGC GCA TGC TAC GAG ATC AAG TGC        96
Ile Phe Lys Asp Gly Leu Gly Cys Gly Ala Cys Tyr Glu Ile Lys Cys
                20                  25                  30

AAG GAA CCC GTC GAG TGC TCC GGC GAG CCC GTC CTC GTC AAG ATC ACC       144
Lys Glu Pro Val Glu Cys Ser Gly Glu Pro Val Leu Val Lys Ile Thr
            35                  40                  45

GAC AAG AAC TAC GAG CAC ATC GCC GCC TAC CAC TTC GAC CTC TCC GGC       192
Asp Lys Asn Tyr Glu His Ile Ala Ala Tyr His Phe Asp Leu Ser Gly
        50                  55                  60

AAG GCC TTC GGC GCC ATG GCC AAG AAG GGC CAG GAA GAC AAG CTG CGC       240
Lys Ala Phe Gly Ala Met Ala Lys Lys Gly Gln Glu Asp Lys Leu Arg
 65                  70                  75                  80

AAG GCC GGT GAG CTG ACT CTG CAG TTC CGC CGC GTC AAG TGC AAG TAC       288
Lys Ala Gly Glu Leu Thr Leu Gln Phe Arg Arg Val Lys Cys Lys Tyr
                85                  90                  95

CCC TCC GGC ACC AAG ATC ACC TTC CAC ATC GAG AAG GGA TCC AAC GAC       336
Pro Ser Gly Thr Lys Ile Thr Phe His Ile Glu Lys Gly Ser Asn Asp
                100                 105                 110

CAT TAC CTG GCG CTG CTC GTC AAG TAC GCC GCC GGC GAT GGC AAC ATT       384
His Tyr Leu Ala Leu Leu Val Lys Tyr Ala Ala Gly Asp Gly Asn Ile
            115                 120                 125

GTC GCC GTC GAC ATC AAG CCC AAG GAC TCC GAC GAG TTC ATT CCC ATG       432
Val Ala Val Asp Ile Lys Pro Lys Asp Ser Asp Glu Phe Ile Pro Met
        130                 135                 140

AAG TCG TCC TGG GGC GCC ATC TGG AGG ATC GAC CCC AAG AAG CCG CTC       480
Lys Ser Ser Trp Gly Ala Ile Trp Arg Ile Asp Pro Lys Lys Pro Leu
145                 150                 155                 160

AAG GGC CCC TTC TCC ATC CGC CTC ACC TCC GAG GGC GGC GCC CAT CTC       528
Lys Gly Pro Phe Ser Ile Arg Leu Thr Ser Glu Gly Gly Ala His Leu
                165                 170                 175

GTC CAG GAC GAC GTC ATC CCA GCC AAC TGG AAG CCA GAC ACC GTC TAC       576
Val Gln Asp Asp Val Ile Pro Ala Asn Trp Lys Pro Asp Thr Val Tyr
                180                 185                 190

ACC TCC AAG CTC CAG TTC GGA GCC TGAGAGACGA TGATCCTCCA TGCATATCCT      630
Thr Ser Lys Leu Gln Phe Gly Ala
            195                 200

CGCCGATTGC AAGGGCTCAT ATATGACATG TGCGTGTACG CATCTGTCGA ATAAGCATCC     690

ATATATGCAT GAGTTTAATA TTTCTTTTTA TTTCCCCCCT TCAATTATAT GTACATCTCA     750

ATGTGGAGAG TTATTTTCTC GTGCC                                           775

(2) INFORMATION FOR SEQ ID NO: 4:

(i) SEQUENCE CHARACTERISTICS:
        (A) LENGTH: 200 amino acids
        (B) TYPE: amino acid
        (D) TOPOLOGY: linear (ii) MOLECULE TYPE: protein (xi) SEQUENCE DESCRIPTION: SEQ ID NO: 4:

Val Asp Lys Pro Pro Phe Asp Gly Met Thr Ala Cys Gly Asn Glu Pro
 1               5                  10                  15

Ile Phe Lys Asp Gly Leu Gly Cys Gly Ala Cys Tyr Glu Ile Lys Cys
                20                  25                  30
```

```
Lys Glu Pro Val Glu Cys Ser Gly Glu Pro Val Leu Val Lys Ile Thr
             35                  40                  45

Asp Lys Asn Tyr Glu His Ile Ala Ala Tyr His Phe Asp Leu Ser Gly
 50                  55                  60

Lys Ala Phe Gly Ala Met Ala Lys Lys Gly Gln Glu Asp Lys Leu Arg
 65                  70                  75                  80

Lys Ala Gly Glu Leu Thr Leu Gln Phe Arg Arg Val Lys Cys Lys Tyr
                 85                  90                  95

Pro Ser Gly Thr Lys Ile Thr Phe His Ile Glu Lys Gly Ser Asn Asp
                100                 105                 110

His Tyr Leu Ala Leu Leu Val Lys Tyr Ala Ala Gly Asp Gly Asn Ile
                115                 120                 125

Val Ala Val Asp Ile Lys Pro Lys Asp Ser Asp Glu Phe Ile Pro Met
    130                 135                 140

Lys Ser Ser Trp Gly Ala Ile Trp Arg Ile Asp Pro Lys Lys Pro Leu
145                 150                 155                 160

Lys Gly Pro Phe Ser Ile Arg Leu Thr Ser Glu Gly Gly Ala His Leu
                165                 170                 175

Val Gln Asp Asp Val Ile Pro Ala Asn Trp Lys Pro Asp Thr Val Tyr
                180                 185                 190

Thr Ser Lys Leu Gln Phe Gly Ala
                195                 200

(2) INFORMATION FOR SEQ ID NO: 5:

(i) SEQUENCE CHARACTERISTICS:
        (A) LENGTH: 197 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 5:

Asp Lys Pro Pro Phe Asp Gly Met Thr Ala Cys Gly Asn Glu Pro Ile
 1               5                  10                  15

Phe Lys Asp Gly Leu Gly Cys Gly Ala Cys Tyr Glu Ile Lys Cys Lys
                 20                  25                  30

Glu Pro Val Glu Cys Ser Gly Glu Pro Val Leu Val Lys Ile Thr Asp
                 35                  40                  45

Lys Asn Tyr Glu His Ile Ala Ala Tyr His Phe Asp Leu Ser Gly Lys
 50                  55                  60

Ala Phe Gly Ala Met Ala Lys Lys Gly Gln Glu Asp Lys Leu Arg Lys
 65                  70                  75                  80

Ala Gly Glu Leu Thr Leu Gln Phe Arg Arg Val Lys Cys Lys Tyr Pro
                 85                  90                  95

Ser Gly Thr Lys Ile Thr Phe His Ile Glu Lys Gly Ser Asn Asp His
                100                 105                 110

Tyr Leu Ala Leu Leu Val Lys Tyr Ala Ala Gly Asp Gly Asn Ile Val
                115                 120                 125

Ala Val Asp Ile Lys Pro Lys Asp Ser Asp Glu Phe Ile Pro Met Lys
    130                 135                 140

Ser Ser Trp Gly Ala Ile Trp Arg Ile Asp Pro Lys Lys Pro Leu Lys
145                 150                 155                 160

Gly Pro Phe Ser Ile Arg Leu Thr Ser Glu Gly Gly Ala His Leu Val
                165                 170                 175
```

Gln Asp Asp Val Ile Pro Ala Asn Trp Lys Pro Asp Thr Val Tyr Thr
        180                 185                 190

Ser Lys Leu Gln Phe
        195

(2) INFORMATION FOR SEQ ID NO: 6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

TTGAATTCGA CACGGCGGAA CTGCAGCAT                                             29

(2) INFORMATION FOR SEQ ID NO: 7:

(i) SEQUENCE CHARACTERISTICS:
        (A) LENGTH: 138 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 7:

Asp Leu Ser Gly Lys Ala Phe Gly Ala Met Ala Lys Lys Gly Glu Glu
1               5                   10                  15

Asp Lys Leu Arg Lys Ala Gly Glu Leu Met Leu Gln Phe Arg Arg Val
            20                  25                  30

Lys Cys Glu Tyr Pro Ser Asp Thr Lys Ile Ala Phe His Val Glu Lys
        35                  40                  45

Gly Ser Asn Pro Asn Tyr Leu Ala Leu Leu Val Lys Tyr Ala Ala Gly
    50                  55                  60

Asp Gly Asn Ile Val Ser Val Asp Ile Lys Ser Lys Gly Ser Asp Asp
65                  70                  75                  80

Phe Leu Pro Met Lys Gln Ser Trp Gly Ala Ile Trp Arg Ile Asp Pro
                85                  90                  95

Pro Lys Pro Leu Lys Gly Pro Phe Thr Ile Arg Leu Thr Ser Glu Ser
            100                 105                 110

Gly Gly His Val Glu Gln Glu Asp Val Ile Pro Glu Asp Trp Lys Pro
        115                 120                 125

Asp Thr Val Tyr Lys Ser Lys Ile Gln Phe
        130                 135

(2) INFORMATION FOR SEQ ID NO: 8:

(i) SEQUENCE CHARACTERISTICS:
        (A) LENGTH: 86 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 8:

Leu Ala Leu Leu Val Lys Tyr Ala Ala Gly Asp Gly Asn Ile Val Ala
1               5                   10                  15

```
Val Asp Ile Lys Pro Lys Asp Ser Asp Glu Phe Ile Pro Met Lys Ser
            20                  25                  30

Ser Trp Gly Ala Ile Trp Arg Ile Asp Pro Lys Pro Leu Lys Gly
            35                  40                  45

Pro Phe Ser Ile Arg Leu Thr Ser Glu Gly Gly Ala His Leu Val Gln
        50                  55                  60

Asp Asp Val Ile Pro Ala Asn Trp Lys Pro Asp Thr Val Tyr Thr Ser
65                  70                  75                  80

Lys Leu Gln Phe Gly Ala
                85

(2) INFORMATION FOR SEQ ID NO: 9:

(i) SEQUENCE CHARACTERISTICS:
        (A) LENGTH: 68 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 9:

Ile Lys Pro Lys Asp Ser Asp Glu Phe Ile Pro Met Lys Ser Ser Trp
1               5                   10                  15

Gly Ala Ile Trp Arg Ile Asp Pro Lys Pro Leu Lys Gly Pro Phe
            20                  25                  30

Ser Ile Arg Leu Thr Ser Glu Gly Gly Ala His Leu Val Gln Asp Asp
            35                  40                  45

Val Ile Pro Ala Asn Trp Lys Pro Asp Thr Val Tyr Thr Ser Lys Leu
        50                  55                  60

Gln Phe Gly Ala
65

(2) INFORMATION FOR SEQ ID NO: 10:

(i) SEQUENCE CHARACTERISTICS:
        (A) LENGTH: 263 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 41..262

(xi) SEQUENCE DESCRIPTION: SEQ ID NO: 10:

ATTGATCATT GGAATCCATT ACATACAGAA GCAGCAAGAA ATG GCG CAC ACG AAA      55
                                            Met Ala His Thr Lys
                                            1               5

CTG GCG CTG GTT GCG GTG CTT GTG GCT GCG ATG GTG GCC GGG CGG GTC    103
Leu Ala Leu Val Ala Val Leu Val Ala Ala Met Val Ala Gly Arg Val
                10                  15                  20

GTG GCC ATC GGC GAC AAG CCA GGG CCC AAC ATC ACG GCG ACC TAC GGC    151
Val Ala Ile Gly Asp Lys Pro Gly Pro Asn Ile Thr Ala Thr Tyr Gly
            25                  30                  35

AAC AAG TGG CTG GAG GCC AAG GCC ACT TTC TAC GGT AGC AAC CCA CGC    199
Asn Lys Trp Leu Glu Ala Lys Ala Thr Phe Tyr Gly Ser Asn Pro Arg
        40                  45                  50

GGT GCC GCC CCC GAT GAC CAC GGC GGC GCT TGC GGG TAC AAG GAC GTC    247
```

```
Gly Ala Ala Pro Asp Asp His Gly Gly Ala Cys Gly Tyr Lys Asp Val
        55                  60                  65

GAC AAG CCT CCC TTC G                                                    263
Asp Lys Pro Pro Phe
 70
```

(2) INFORMATION FOR SEQ ID NO: 11:

(i) SEQUENCE CHARACTERISTICS:
        (A) LENGTH: 74 amino acids
        (B) TYPE: amino acid
        (D) TOPOLOGY: linear (ii) MOLECULE TYPE: protein (xi) SEQUENCE DESCRIPTION: SEQ ID NO: 11:

```
Met Ala His Thr Lys Leu Ala Leu Val Ala Val Leu Val Ala Ala Met
 1               5                  10                  15

Val Ala Gly Arg Val Val Ala Ile Gly Asp Lys Pro Gly Pro Asn Ile
            20                  25                  30

Thr Ala Thr Tyr Gly Asn Lys Trp Leu Glu Ala Lys Ala Thr Phe Tyr
        35                  40                  45

Gly Ser Asn Pro Arg Gly Ala Ala Pro Asp Asp His Gly Gly Ala Cys
    50                  55                  60

Gly Tyr Lys Asp Val Asp Lys Pro Pro Phe
 65                  70
```

(2) INFORMATION FOR SEQ ID NO: 12:

(i) SEQUENCE CHARACTERISTICS:
        (A) LENGTH: 262 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 28..261

(xi) SEQUENCE DESCRIPTION: SEQ ID NO: 12:

```
GTCCGATCGA TCATTCACAA GCAAGAA ATG GCG CAG ACC ACG ATG AAT CAG          51
                              Met Ala Gln Thr Thr Met Asn Gln
                               1               5

AAA CTG GCG CTG GTT GCG TGG CCC GTG GCT GCG ATG GTG GCC GGG CGG        99
Lys Leu Ala Leu Val Ala Trp Pro Val Ala Ala Met Val Ala Gly Arg
         10                  15                  20

GTC GTG GCC ATC GGC GAC AAG CCA GGG CCC AAC ATC ACA GCG ACC TAC       147
Val Val Ala Ile Gly Asp Lys Pro Gly Pro Asn Ile Thr Ala Thr Tyr
 25                  30                  35                  40

GGC AGC AAG TGG CTG GAG GCC AAG GCC ACC TTC TAC GGC AGC AAC CCG       195
Gly Ser Lys Trp Leu Glu Ala Lys Ala Thr Phe Tyr Gly Ser Asn Pro
             45                  50                  55

CGC GGT GCC GCC CCC GAT GAC CAC GGC GGC GCT TGC GGG TAC AAG GAC       243
Arg Gly Ala Ala Pro Asp Asp His Gly Gly Ala Cys Gly Tyr Lys Asp
         60                  65                  70

GTC GAC AAG CCT CCC TTC G                                             262
Val Asp Lys Pro Pro Phe
         75
```

(2) INFORMATION FOR SEQ ID NO: 13:

(i) SEQUENCE CHARACTERISTICS:

(A) LENGTH: 78 amino acids
        (B) TYPE: amino acid
        (D) TOPOLOGY: linear (ii) MOLECULE TYPE: protein (xi) SEQUENCE DESCRIPTION: SEQ ID NO: 13:

Met Ala Gln Thr Thr Met Asn Gln Lys Leu Ala Leu Val Ala Trp Pro
1               5                   10                  15

Val Ala Ala Met Val Ala Gly Arg Val Val Ala Ile Gly Asp Lys Pro
            20                  25                  30

Gly Pro Asn Ile Thr Ala Thr Tyr Gly Ser Lys Trp Leu Glu Ala Lys
            35                  40                  45

Ala Thr Phe Tyr Gly Ser Asn Pro Arg Gly Ala Ala Pro Asp His
        50                  55                  60

Gly Gly Ala Cys Gly Tyr Lys Asp Val Asp Lys Pro Pro Phe
65              70                  75

(2) INFORMATION FOR SEQ ID NO: 14:

(i) SEQUENCE CHARACTERISTICS:
        (A) LENGTH: 78 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 3
        (D) OTHER INFORMATION: /note= "Xaa is an unknown amino acid"

(ix) FEATURE:
        (A) NAME/KEY: Modified-site
        (B) LOCATION: 5-8
        (D) OTHER INFORMATION: /note= "Xaa is an unknown amino acid"

(ix) FEATURE:
        (A) NAME/KEY: Modified-site
        (B) LOCATION: 15-16
        (D) OTHER INFORMATION: /note= "Xaa is an unknown amino acid"

(ix) FEATURE:
        (A) NAME/KEY: Modified-site
        (B) LOCATION: 42
        (D) OTHER INFORMATION: /note= "Xaa is an unknown amino acid"

(ix) FEATURE:
        (A) NAME/KEY: Modified-site
        (B) LOCATION: 71-72
        (D) OTHER INFORMATION: /note= "Xaa is an unknown amino acid"

(xi) SEQUENCE DESCRIPTION: SEQ ID NO: 14:

Met Ala Xaa Thr Xaa Xaa Xaa Xaa Lys Leu Ala Leu Val Ala Xaa Xaa
1               5                   10                  15

Val Ala Ala Met Val Ala Gly Arg Val Val Ala Ile Gly Asp Lys Pro
            20                  25                  30

Gly Pro Asn Ile Thr Ala Thr Tyr Gly Xaa Lys Trp Leu Glu Ala Lys
            35                  40                  45

Ala Thr Phe Tyr Gly Ser Asn Pro Arg Gly Ala Ala Pro Asp His
        50                  55                  60

Gly Gly Ala Cys Gly Tyr Xaa Xaa Val Asp Lys Pro Pro Phe
65              70                  75

(2) INFORMATION FOR SEQ ID NO: 15:

```
    (i) SEQUENCE CHARACTERISTICS:
        (A) LENGTH: 272 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 3
        (D) OTHER INFORMATION: /note= "Xaa is an unknown amino acid"

(ix) FEATURE:
        (A) NAME/KEY: Modified-site
        (B) LOCATION: 5-8
        (D) OTHER INFORMATION: /note= "Xaa is an unknown amino acid"

(ix) FEATURE:
        (A) NAME/KEY: Modified-site
        (B) LOCATION: 15-16
        (D) OTHER INFORMATION: /note= "Xaa is an unknown amino acid"

(ix) FEATURE:
        (A) NAME/KEY: Modified-site
        (B) LOCATION: 42
        (D) OTHER INFORMATION: /note= "Xaa is an unknown amino acid"

(ix) FEATURE:
        (A) NAME/KEY: Modified-site
        (B) LOCATION: 71-72
        (D) OTHER INFORMATION: /note= "Xaa is an unknown amino acid"

(xi) SEQUENCE DESCRIPTION: SEQ ID NO: 15:

Met Ala Xaa Thr Xaa Xaa Xaa Xaa Lys Leu Ala Leu Val Ala Xaa Xaa
1               5                   10                  15

Val Ala Ala Met Val Ala Gly Arg Val Val Ala Ile Gly Asp Lys Pro
            20                  25                  30

Gly Pro Asn Ile Thr Ala Thr Tyr Gly Xaa Lys Trp Leu Glu Ala Lys
        35                  40                  45

Ala Thr Phe Tyr Gly Ser Asn Pro Arg Gly Ala Ala Pro Asp His
    50                  55                  60

Gly Gly Ala Cys Gly Tyr Xaa Xaa Val Asp Lys Pro Pro Phe Asp Gly
65              70                  75                  80

Met Thr Ala Cys Gly Asn Glu Pro Ile Phe Lys Asp Gly Leu Gly Cys
                85                  90                  95

Gly Ala Cys Tyr Glu Ile Lys Cys Lys Glu Pro Val Glu Cys Ser Gly
                100                 105                 110

Glu Pro Val Leu Val Lys Ile Thr Asp Lys Asn Tyr Glu His Ile Ala
            115                 120                 125

Ala Tyr His Phe Asp Leu Ser Gly Lys Ala Phe Gly Ala Met Ala Lys
    130                 135                 140

Lys Gly Gln Glu Asp Lys Leu Arg Lys Ala Gly Glu Leu Thr Leu Gln
145                 150                 155                 160

Phe Arg Arg Val Lys Cys Lys Tyr Pro Ser Gly Thr Lys Ile Thr Phe
                165                 170                 175

His Ile Glu Lys Gly Ser Asn Asp His Tyr Leu Ala Leu Leu Val Lys
                180                 185                 190

Tyr Ala Ala Gly Asp Gly Asn Ile Val Ala Val Asp Ile Lys Pro Lys
        195                 200                 205

Asp Ser Asp Glu Phe Ile Pro Met Lys Ser Ser Trp Gly Ala Ile Trp
210                 215                 220
```

```
Arg Ile Asp Pro Lys Lys Pro Leu Lys Gly Pro Phe Ser Ile Arg Leu
225                 230                 235                 240

Thr Ser Glu Gly Gly Ala His Leu Val Gln Asp Asp Val Ile Pro Ala
                245                 250                 255

Asn Trp Lys Pro Asp Thr Val Tyr Thr Ser Lys Leu Gln Phe Gly Ala
                260                 265                 270
```

(2) INFORMATION FOR SEQ ID NO: 16:

(i) SEQUENCE CHARACTERISTICS:
        (A) LENGTH: 145 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 58
        (D) OTHER INFORMATION: /note= "Xaa is an unknown amino acid"

(ix) FEATURE:
        (A) NAME/KEY: Modified-site
        (B) LOCATION: 77
        (D) OTHER INFORMATION: /note= "Xaa is an unknown amino acid"

(ix) FEATURE:
        (A) NAME/KEY: Modified-site
        (B) LOCATION: 87
        (D) OTHER INFORMATION: /note= "Xaa is an unknown amino acid"

(ix) FEATURE:
        (A) NAME/KEY: Modified-site
        (B) LOCATION: 126
        (D) OTHER INFORMATION: /note= "Xaa is an unknown amino acid"

(xi) SEQUENCE DESCRIPTION: SEQ ID NO: 16:

```
His Ile Ala Ala Tyr His Phe Asp Leu Ser Gly Lys Ala Phe Gly Ala
1               5                   10                  15

Met Ala Lys Lys Gly Glu Glu Asp Lys Leu Arg Lys Ala Gly Glu Leu
                20                  25                  30

Met Leu Gln Phe Arg Arg Val Lys Cys Glu Tyr Pro Ser Asp Thr Lys
                35                  40                  45

Ile Ala Phe His Val Glu Lys Gly Ser Xaa Pro Asn Tyr Leu Ala Leu
    50                  55                  60

Leu Val Lys Tyr Ala Ala Gly Asp Gly Asn Ile Val Xaa Val Asp Ile
65                  70                  75                  80

Lys Xaa Lys Gly Ser Asp Xaa Phe Leu Pro Met Lys Gln Ser Trp Gly
                85                  90                  95

Ala Ile Trp Arg Ile Asp Pro Pro Lys Pro Leu Lys Gly Pro Phe Thr
                100                 105                 110

Ile Arg Leu Thr Ser Glu Ser Gly Gly His Val Glu Gln Xaa Asp Val
                115                 120                 125

Ile Pro Glu Asp Trp Lys Pro Asp Thr Val Tyr Lys Ser Lys Ile Gln
    130                 135                 140

Phe
145
```

(2) INFORMATION FOR SEQ ID NO: 17:

(i) SEQUENCE CHARACTERISTICS:
        (A) LENGTH: 594 base pairs
        (B) TYPE: nucleic acid (C) STRANDEDNESS: single
        (D) TOPOLOGY: linear (ii) MOLECULE TYPE: cDNA (xi) SEQUENCE DESCRIPTION: SEQ ID NO: 17:

```
GACCTTTCTG GCAAGGCGTT CGGCGCCATG GCCAAGAAGG GCGAGGAGGA CAAGCTGCGC      60

AAGGCCGGCG AGCTGATGCT GCAGTTCCGC CGCGTCAAGT GCGAGTACCC ATCCGACACC     120

AAGATCGCCT TCCACGTTGA GAAGGGCTCC AACCCCAATT ACCTGGCGCT GCTCGTGAAG     180

TACGCGGCCG GCGACGGCAA TATCGTCAGT GTCGATATCA AGTCCAAGGG CTCCGACGAC     240

TTCCTGCCCA TGAAGCAGTC GTGGGGCGCC ATCTGGAGGA TCGATCCCCC CAAGCCGCTC     300

AAGGGTCCCT TCACGATCCG CCTCACCAGC GAGAGTGGCG GCCATGTCGA ACAGGAAGAT     360

GTCATCCCCG AAGACTGGAA GCCCGACACC GTCTACAAGT CCAAGATCCA GTTCTGAGCC     420

TGATGTGCCC ACAAACAGCG TGCACACTAA TAACACAACC TTATGACATC TTTGTTTCTT     480

TTTTGCAAGA AACAGTCTAT GCGATCTGCA TGCATGCATA CATATAATAA CAAGTATCGA     540

TGCGCGCGTG AGGTTTTTCT CTCCTTTTCT TTCTACTATT ATTGTTGCAT TTCC          594
```

(2) INFORMATION FOR SEQ ID NO: 18:

(i) SEQUENCE CHARACTERISTICS:
        (A) LENGTH: 802 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

```
GACAAGCCTC CCTTCGACGG CATGACCGCC TGCGGCAACG AGCCCATCTT CAAGGACGGC      60

CTCGGCTGCG GCGCATGCTA CGAGATCAAG TGCAAGGAAC CCGTCGAGTG CTCCGGCGAG     120

CCCGTCCTCG TCAAGATCAC CGACAAGAAC TACGAGCACA TCGCCGCCTA CCACTTCGAC     180

CTCTCCGGCA AGGCCTTCGG CGCCATGGCC AAGAAGGGCC AGGAAGACAA GCTGCGCAAG     240

GCCGGTGAGC TGACTCTGCA GTTCCGCCGC GTCAAGTGCA AGTACCCCTC CGGCACCAAG     300

ATCACCTTCC ACATCGAGAA GGGATCCAAC GACCATTACC TGGCGCTGCT CGTCAAGTAC     360

GCGGCCGGCG ATGGCAACAT TGTTGCTGTC GACATCAAGC CCAAGGACTC CGACGAGTTC     420

ATTCCCATGA AGTCGTCCTG GGGCGCCATC TGGAGGATCG ACCCCAAGAA GCCGCTCAAG     480

GGCCCCTTCT CCATCCGCCT CACCTCCGAG GGCGGCGCCC ATCTCGTCCA AGACGACGTC     540

ATCCCAGCCA ACTGGAAGCC AGACACCGTC TACACCTCCA AGTCCAGTT CTAAACACGC      600

AAAGGCTTAT ATTTGGAGCA TATGAAGAAT GCACACAAGC ATGTGCTTCA GCTTCTCTTT     660

TCTTTACTTT CCTTCATTGC ATTGCATCTC ATCATCTCCA TATGTTTTTT AGATTTTGTG     720

ATGCAAAGTG TCATAAGTGC CAAGGATTCA GGAGGCGCTT TAAGCAGTGT CGAGGATGTA     780

GGGATCTCGT GCCGCTCGTG CC                                             802
```

(2) INFORMATION FOR SEQ ID NO: 19:

(i) SEQUENCE CHARACTERISTICS:
        (A) LENGTH: 832 base pairs
        (B) TYPE: nucleic acid
        (C) STRANDEDNESS: single
        (D) TOPOLOGY: linear (ii) MOLECULE TYPE: cDNA -continued (xi) SEQUENCE DESCRIPTION: SEQ ID NO: 19:

```
CGACAAGCCT CCCTTCGACG GCATGACCGC CTGCGGCAAC GAGCCCATCT TCAAGGACGG      60
CCTCGGCTGC GGCGCATGCT ACGAGATCAA GTGCAAGGAA CCCGTCGAGT GCTCCGGCGA     120
GCCCGTCCTC GTCAAGATCA CCGACAAGAA CTACGAGCAC ATCGCCGCCT ACCACTTCGA     180
CCTCTCCGGC AAGGCCTTCG GCGCCATGGC CAAGAAGGGC CAGGAAGACA AGCTGCGCAA     240
GGCCGGTGAG CTGACTCTGC AGTTCCGCCG CGTCAAGTGC AAGTACCCCT CCGGCACCAA     300
GATCACCTTC CACATCGAGA AGGGATCCAA CGACCATTAC CTGGCGCTGC TCGTCAAGTA     360
CGCCGCCGGC GATGGCAACA TTGTCGCCGT CGACATCAAG CCCAAGGACT CCGACGAGTT     420
CATTCCCATG AAGTCGTCCT GGGGCGCCAT CTGGAGGATC GACCCCAAGA AGCCGCTCAA     480
GGGCCCCTTC TCCATCCGCC TCACCTCCGA GGGCGGCGCC CATCTCGTCC AGGACGACGT     540
CATCCCAGCC AACTGGAAGC CAGACACCGT CTACACCTCC AAGCTCCAGT TCTAAACACG     600
CAAAGGCTTA TATTTGGAGC ATATGAAGAA TGCTCTCAAG CATGTGCTTC AGGAGTGCCC     660
ACGATGTAGG GATAACCGAT TCATCAAAGC ACATCATGTG AAACATCAGT TGAAAAAACT     720
GGTTGATTTT TTTATTATTA TCGTGTAGAT TTGGATGCTT TTGAAATCTT TTGTATTCTT     780
CATTGAGTTT ACAAAATTAC GCAATTGATG AGAGATGCCC TCTTGCATTT TT            832
```

(2) INFORMATION FOR SEQ ID NO: 20:

(i) SEQUENCE CHARACTERISTICS:
        (A) LENGTH: 759 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..738

(ix) FEATURE:
        (A) NAME/KEY: CDS
        (B) LOCATION: 742..759

(xi) SEQUENCE DESCRIPTION: SEQ ID NO: 20:

```
GCC ATC GGC GAC AAG CCA GGG CCC AAC ATC ACG GCG ACC TAC GGC AGC       48
Ala Ile Gly Asp Lys Pro Gly Pro Asn Ile Thr Ala Thr Tyr Gly Ser
 1               5                  10                  15

AAG TGG CTG GAG GCC AGG GCC ACC TTC TAC GGC AGC AAC CCG CGC GGT       96
Lys Trp Leu Glu Ala Arg Ala Thr Phe Tyr Gly Ser Asn Pro Arg Gly
            20                  25                  30

GCC GCC CCC GAT GAC CAC GGC GGC GCT TGC GGG TAC AAG GAC GTC GAC      144
Ala Ala Pro Asp Asp His Gly Gly Ala Cys Gly Tyr Lys Asp Val Asp
        35                  40                  45

AAG CCT CCC TTC GAC GGC ATG ACC GCC TGC GGC AAC GAG CCC ATC TTC      192
Lys Pro Pro Phe Asp Gly Met Thr Ala Cys Gly Asn Glu Pro Ile Phe
    50                  55                  60

AAG GAC GGC CTC GGC TGC GGC GCA TGC TAC GAG ATC AAG TGC AAG GAA      240
Lys Asp Gly Leu Gly Cys Gly Ala Cys Tyr Glu Ile Lys Cys Lys Glu
65                  70                  75                  80

CCC GTC GAG TGC TCC GGC GAG CCC GTC CTC GTC AAG ATC ACC GAC AAG      288
Pro Val Glu Cys Ser Gly Glu Pro Val Leu Val Lys Ile Thr Asp Lys
                85                  90                  95

AAC TAC GAG CAC ATC GCC GCC TAC CAC TTC GAC CTC TCC GGC AAG GCC      336
Asn Tyr Glu His Ile Ala Ala Tyr His Phe Asp Leu Ser Gly Lys Ala
            100                 105                 110
```

```
TTC GGC GCC ATG GCC AAG AAG GGC CAG GAA GAC AAG CTG CGC AAG GCC      384
Phe Gly Ala Met Ala Lys Lys Gly Gln Glu Asp Lys Leu Arg Lys Ala
            115                 120                 125

GGT GAG CTG ACT CTG CAG TTC CGC CGC GTC AAG TGC AAG TAC CCC TCC      432
Gly Glu Leu Thr Leu Gln Phe Arg Arg Val Lys Cys Lys Tyr Pro Ser
130                 135                 140

GGC ACC AAG ATC ACC TTC CAC ATC GAG AAG GGA TCC AAC GAC CAT TAC      480
Gly Thr Lys Ile Thr Phe His Ile Glu Lys Gly Ser Asn Asp His Tyr
145                 150                 155                 160

CTG GCG CTG CTC GTC AAG TAC GCG GCC GGC GAT GGC AAC ATT GTC GCC      528
Leu Ala Leu Leu Val Lys Tyr Ala Ala Gly Asp Gly Asn Ile Val Ala
                165                 170                 175

GTC GAC ATC AAG CCC AGG GAC TCC GAC GAG TTC ATT CCC ATG AAG TCG      576
Val Asp Ile Lys Pro Arg Asp Ser Asp Glu Phe Ile Pro Met Lys Ser
            180                 185                 190

TCC TGG GGC GCC ATC TGG AGG ATC GAC CCC AAG AAG CCG CTC AAG GGC      624
Ser Trp Gly Ala Ile Trp Arg Ile Asp Pro Lys Lys Pro Leu Lys Gly
            195                 200                 205

CCC TTC TCC ATC CGC CTC ACC TCC GAG GGC GGC GCC CAT CTC GTC CAG      672
Pro Phe Ser Ile Arg Leu Thr Ser Glu Gly Gly Ala His Leu Val Gln
210                 215                 220

GAC GAC GTC ATC CCA GCC AAC TGG AAG CCA GAC ACC GTC TAC ACC TCC      720
Asp Asp Val Ile Pro Ala Asn Trp Lys Pro Asp Thr Val Tyr Thr Ser
225                 230                 235                 240

AAG CTC CAG TTC GGA GCC TGA GAG ACG ATG ATC CTC CAT                  759
Lys Leu Gln Phe Gly Ala
                245

(2) INFORMATION FOR SEQ ID NO: 21:

(i) SEQUENCE CHARACTERISTICS:
        (A) LENGTH: 246 amino acids
        (B) TYPE: amino acid
        (D) TOPOLOGY: linear (ii) MOLECULE TYPE: protein (xi) SEQUENCE DESCRIPTION: SEQ ID NO: 21:

Ala Ile Gly Asp Lys Pro Gly Pro Asn Ile Thr Ala Thr Tyr Gly Ser
1               5                   10                  15

Lys Trp Leu Glu Ala Arg Ala Thr Phe Tyr Gly Ser Asn Pro Arg Gly
            20                  25                  30

Ala Ala Pro Asp Asp His Gly Gly Ala Cys Gly Tyr Lys Asp Val Asp
            35                  40                  45

Lys Pro Pro Phe Asp Gly Met Thr Ala Cys Gly Asn Glu Pro Ile Phe
        50                  55                  60

Lys Asp Gly Leu Gly Cys Gly Ala Cys Tyr Glu Ile Lys Cys Lys Glu
65                  70                  75                  80

Pro Val Glu Cys Ser Gly Glu Pro Val Leu Val Lys Ile Thr Asp Lys
                85                  90                  95

Asn Tyr Glu His Ile Ala Ala Tyr His Phe Asp Leu Ser Gly Lys Ala
            100                 105                 110

Phe Gly Ala Met Ala Lys Lys Gly Gln Glu Asp Lys Leu Arg Lys Ala
            115                 120                 125

Gly Glu Leu Thr Leu Gln Phe Arg Arg Val Lys Cys Lys Tyr Pro Ser
        130                 135                 140

Gly Thr Lys Ile Thr Phe His Ile Glu Lys Gly Ser Asn Asp His Tyr
145                 150                 155                 160

Leu Ala Leu Leu Val Lys Tyr Ala Ala Gly Asp Gly Asn Ile Val Ala
```

```
                    165                 170                 175
Val Asp Ile Lys Pro Arg Asp Ser Asp Glu Phe Ile Pro Met Lys Ser
            180                 185                 190

Ser Trp Gly Ala Ile Trp Arg Ile Asp Pro Lys Pro Leu Lys Gly
        195                 200                 205

Pro Phe Ser Ile Arg Leu Thr Ser Glu Gly Ala His Leu Val Gln
    210                 215                 220

Asp Asp Val Ile Pro Ala Asn Trp Lys Pro Asp Thr Val Tyr Thr Ser
225                 230                 235                 240

Lys Leu Gln Phe Gly Ala
            245

(2) INFORMATION FOR SEQ ID NO: 22:

(i) SEQUENCE CHARACTERISTICS:
        (A) LENGTH: 368 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..368

(xi) SEQUENCE DESCRIPTION: SEQ ID NO: 22:

CC AAC ATC ACT GCA ACC TAC GGT GAC AAG TGG CTG GAT GCG AAG GCC        47
   Asn Ile Thr Ala Thr Tyr Gly Asp Lys Trp Leu Asp Ala Lys Ala
   1               5                   10                  15

ACG TTC TAC GGC AGC GAC CCA CGT GGC GCG GCC CCC GAT GAC CAT GGC       95
Thr Phe Tyr Gly Ser Asp Pro Arg Gly Ala Ala Pro Asp Asp His Gly
                20                  25                  30

GGC GCG TGC GGA TAC AAG GAC GTC GAC AAG GCA CCC TTC GAC AGC ATG       143
Gly Ala Cys Gly Tyr Lys Asp Val Asp Lys Ala Pro Phe Asp Ser Met
            35                  40                  45

ACT GGA TGC GGC AAC GAG CCC ATC TTC AAG GAC GGT CTG GGC TGC GGC       191
Thr Gly Cys Gly Asn Glu Pro Ile Phe Lys Asp Gly Leu Gly Cys Gly
        50                  55                  60

TCC TGC TAC GAG ATC AAG TGC AAG GAG CCA GCC GAG TGC TCA GGC GAG       239
Ser Cys Tyr Glu Ile Lys Cys Lys Glu Pro Ala Glu Cys Ser Gly Glu
65                  70                  75

CCC GTC CTC ATT AAG ATC ACC GAC AAG AAC TAC GAG CAC ATC GCC GCC       287
Pro Val Leu Ile Lys Ile Thr Asp Lys Asn Tyr Glu His Ile Ala Ala
80                  85                  90                  95

TAC CAC TTC GAC CTT TCT GGC AAG GCG TTC GGC GCC ATG GCC AAG AAG       335
Tyr His Phe Asp Leu Ser Gly Lys Ala Phe Gly Ala Met Ala Lys Lys
                100                 105                 110

GGC GAG GAG GAC AAG CTG CGC AAG GCC GGC GAG                           368
Gly Glu Glu Asp Lys Leu Arg Lys Ala Gly Glu
            115                 120

(2) INFORMATION FOR SEQ ID NO: 23:

(i) SEQUENCE CHARACTERISTICS:
        (A) LENGTH: 122 amino acids
        (B) TYPE: amino acid
        (D) TOPOLOGY: linear (ii) MOLECULE TYPE: protein (xi) SEQUENCE DESCRIPTION: SEQ ID NO: 23:

Asn Ile Thr Ala Thr Tyr Gly Asp Lys Trp Leu Asp Ala Lys Ala Thr
```

```
              1               5                  10                 15
            Phe Tyr Gly Ser Asp Pro Arg Gly Ala Ala Pro Asp His Gly Gly
                           20                  25                 30

Ala Cys Gly Tyr Lys Asp Val Asp Lys Ala Pro Phe Asp Ser Met Thr
                           35                  40                 45

Gly Cys Gly Asn Glu Pro Ile Phe Lys Asp Gly Leu Gly Cys Gly Ser
                           50                  55                 60

Cys Tyr Glu Ile Lys Cys Lys Glu Pro Ala Glu Cys Ser Gly Glu Pro
             65                        70                  75                 80

Val Leu Ile Lys Ile Thr Asp Lys Asn Tyr Glu His Ile Ala Ala Tyr
                                  85                  90                 95

His Phe Asp Leu Ser Gly Lys Ala Phe Gly Ala Met Ala Lys Lys Gly
                          100                 105                110

Glu Glu Asp Lys Leu Arg Lys Ala Gly Glu
                          115                 120
```

(2) INFORMATION FOR SEQ ID NO: 24:

(i) SEQUENCE CHARACTERISTICS:
        (A) LENGTH: 245 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 157
        (D) OTHER INFORMATION: /note= "Xaa is Ser or Asn"

(ix) FEATURE:
        (A) NAME/KEY: Modified-site
        (B) LOCATION: 176
        (D) OTHER INFORMATION: /note= "Xaa is Gly or Ser"

(ix) FEATURE:
        (A) NAME/KEY: Modified-site
        (B) LOCATION: 181
        (D) OTHER INFORMATION: /note= "Xaa is Pro or Ser"

(ix) FEATURE:
        (A) NAME/KEY: Modified-site
        (B) LOCATION: 187
        (D) OTHER INFORMATION: /note= "Xaa is Glu or Asp"

(ix) FEATURE:
        (A) NAME/KEY: Modified-site
        (B) LOCATION: 226
        (D) OTHER INFORMATION: /note= "Xaa is Asp or Glu"

(xi) SEQUENCE DESCRIPTION: SEQ ID NO: 24:

```
            Val Ala Ile Xaa Asp Lys Pro Gly Pro Asn Ile Thr Ala Thr Tyr Gly
             1               5                  10                 15

Asp Lys Trp Leu Asp Ala Lys Ala Thr Phe Tyr Gly Ser Asp Pro Arg
                           20                  25                 30

Gly Ala Ala Pro Asp Asp His Gly Gly Ala Cys Gly Tyr Lys Asp Val
                           35                  40                 45

Asp Lys Ala Pro Phe Asp Ser Met Thr Gly Cys Gly Asn Glu Pro Ile
                           50                  55                 60

Phe Lys Asp Gly Leu Gly Cys Gly Ser Cys Tyr Glu Ile Lys Cys Lys
             65                        70                  75                 80

Glu Pro Ala Glu Cys Ser Gly Glu Pro Val Leu Ile Lys Ile Thr Asp
                                  85                  90                 95
```

```
Lys Asn Tyr Glu His Ile Ala Ala Tyr His Phe Asp Leu Ser Gly Lys
            100                 105                 110

Ala Phe Gly Ala Met Ala Lys Lys Gly Glu Glu Asp Lys Leu Arg Lys
            115                 120                 125

Ala Gly Glu Leu Met Leu Gln Phe Arg Arg Val Lys Cys Glu Tyr Pro
            130                 135             140

Ser Asp Thr Lys Ile Ala Phe His Val Glu Lys Gly Ser Xaa Pro Asn
145                 150                 155                 160

Tyr Leu Ala Leu Leu Val Lys Tyr Ala Ala Gly Asp Gly Asn Ile Val
                165                 170                 175

Xaa Val Asp Ile Lys Xaa Lys Gly Ser Asp Xaa Phe Leu Pro Met Lys
            180                 185                 190

Gln Ser Trp Gly Ala Ile Trp Arg Ile Asp Pro Lys Pro Leu Lys
            195                 200             205

Gly Pro Phe Thr Ile Arg Leu Thr Ser Glu Ser Gly Gly His Val Glu
            210                 215                 220

Gln Xaa Asp Val Ile Pro Glu Asp Trp Lys Pro Asp Thr Val Tyr Lys
225                 230                 235                 240

Ser Lys Ile Gln Phe
                245

(2) INFORMATION FOR SEQ ID NO: 25:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 9
        (D) OTHER INFORMATION: /note= "Xaa is an unknown amino acid"

(ix) FEATURE:
        (A) NAME/KEY: Modified-site
        (B) LOCATION: 18
        (D) OTHER INFORMATION: /note= "Xaa is an unknown amino acid"

(xi) SEQUENCE DESCRIPTION: SEQ ID NO:25:

Ala Met Gly Asp Lys Pro Gly Pro Xaa Ile Thr Ala Thr Tyr Gly Asp
1               5                   10                  15

Lys Xaa Leu Asp Ala Lys Thr Ala Phe Asp
            20                  25

(2) INFORMATION FOR SEQ ID NO: 26:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 9
        (D) OTHER INFORMATION: /note= "Xaa is an unknown amino acid"

(ix) FEATURE:
```

(A) NAME/KEY: Modified-site
                (B) LOCATION: 16
                (D) OTHER INFORMATION: /note= "Xaa is an unknown amino acid"

(ix) FEATURE:
                (A) NAME/KEY: Modified-site
                (B) LOCATION: 20
                (D) OTHER INFORMATION: /note= "Xaa is an unknown amino acid"

(xi) SEQUENCE DESCRIPTION: SEQ ID NO: 26:

Ala Ile Gly Asp Lys Pro Gly Pro Xaa Ile Thr Ala Trp Tyr Gly Xaa
1               5                   10                  15

Lys Thr Leu Xaa Ala
            20

(2) INFORMATION FOR SEQ ID NO: 27:

(i) SEQUENCE CHARACTERISTICS:
                (A) LENGTH: 34 amino acids
                (B) TYPE: amino acid
                (D) TOPOLOGY: linear (ii) MOLECULE TYPE: peptide (v) FRAGMENT TYPE: internal (ix) FEATURE:
                (A) NAME/KEY: Modified-site
                (B) LOCATION: 9
                (D) OTHER INFORMATION: /note= "Xaa is an unknown amino acid"

(ix) FEATURE:
                (A) NAME/KEY: Modified-site
                (B) LOCATION: 15-16
                (D) OTHER INFORMATION: /note= "Xaa is an unknown amino acid"

(xi) SEQUENCE DESCRIPTION: SEQ ID NO: 27:

Ala Ile Gly Asp Lys Pro Gly Pro Xaa Ile Thr Ala Thr Tyr Xaa Xaa
1               5                   10                  15

Lys Trp Leu Asp Ala Lys Ala Thr Phe Tyr Gly Ser Asn Pro Arg Gly
            20                  25                  30

Ala Ala (2) INFORMATION FOR SEQ ID NO: 28:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO: 28:

GGGTCTAGAG GTACCGTCCG ATCGATCATT                                      30

(2) INFORMATION FOR SEQ ID NO: 29:

(i) SEQUENCE CHARACTERISTICS:
                (A) LENGTH: 13 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO: 29:

AATGATCGAT GCT                                                        13

(2) INFORMATION FOR SEQ ID NO: 30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 30:

GGGTCTAGAG GTACCGTCCG     20

(2) INFORMATION FOR SEQ ID NO: 31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 31:

GATGTGCTCG TAGTTCTT     18

(2) INFORMATION FOR SEQ ID NO: 32:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 32:

Lys Asn Tyr Glu His Ile
1            5

(2) INFORMATION FOR SEQ ID NO: 33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 33:

GGGGATCCGA GGCCGTCCTT GAAG     24

(2) INFORMATION FOR SEQ ID NO: 34:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 34:

Ile Phe Lys Asp Gly Leu
1            5

(2) INFORMATION FOR SEQ ID NO: 35:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 35:

```
Ala Ile Gly Asp Lys Pro Gly Pro Asn Ile Thr Ala Thr Gly Asn Lys
1               5                   10                  15
Trp Leu Glu Ala Lys Ala Thr Phe Tyr Gly
            20                  25
```

(2) INFORMATION FOR SEQ ID NO: 36:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 36:

```
Ala Ile Gly Asp Lys Pro Gly Pro Asn Ile Thr Ala Thr Gly Ser Lys
1               5                   10                  15
Trp Leu Glu Ala Lys Ala Thr Phe Tyr Gly
            20                  25
```

(2) INFORMATION FOR SEQ ID NO: 37:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 37:

GGGAATTCGC CATCGGCGAC AAGCCAG                                    27

(2) INFORMATION FOR SEQ ID NO: 38:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 38:

CCCTGCAGAT GGAGGATCAT CGTCTC                                    26

(2) INFORMATION FOR SEQ ID NO: 39:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 39:

TTTCTAGAGC CATCGGCGAC AAGCCAGGGC CC                                              32

(2) INFORMATION FOR SEQ ID NO: 40:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 40:

GCGTACTTCA CGAGCAGCGC CAGGTAATT                                                  29

(2) INFORMATION FOR SEQ ID NO: 41:

(i) SEQUENCE CHARACTERISTICS:
            (A) LENGTH: 27 amino acids
            (B) TYPE: amino acid
            (D) TOPOLOGY: linear (ii) MOLECULE TYPE: peptide (v) FRAGMENT TYPE: internal (ix) FEATURE:
            (A) NAME/KEY: Modified-site
            (B) LOCATION: 9
            (D) OTHER INFORMATION: /note= "Xaa is an unknown amino acid"

(xi) SEQUENCE DESCRIPTION: SEQ ID NO: 41:

Ala Met Gly Asp Lys Pro Gly Pro Xaa Ile Thr Ala Thr Tyr Gly Asp
1               5                   10                  15

Lys Trp Leu Asp Ala Lys Ala Thr Phe Tyr Gly
            20                  25

(2) INFORMATION FOR SEQ ID NO: 42:

(i) SEQUENCE CHARACTERISTICS:
            (A) LENGTH: 26 amino acids
            (B) TYPE: amino acid
            (D) TOPOLOGY: linear (ii) MOLECULE TYPE: peptide (v) FRAGMENT TYPE: internal (ix) FEATURE:
            (A) NAME/KEY: Modified-site
            (B) LOCATION: 9
            (D) OTHER INFORMATION: /note= "Xaa is an unknown amino acid"

(ix) FEATURE:
            (A) NAME/KEY: Modified-site
            (B) LOCATION: 18
            (D) OTHER INFORMATION: /note= "Xaa is an unknown amino acid"

(xi) SEQUENCE DESCRIPTION: SEQ ID NO: 42:

Ala Ile Gly Asp Lys Pro Gly Pro Xaa Ile Thr Ala Thr Tyr Gly Ser
1               5                   10                  15

Lys Xaa Leu Glu Ala Lys Ala Thr Phe Tyr
            20                  25

(2) INFORMATION FOR SEQ ID NO: 43:

```
    (i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 9
        (D) OTHER INFORMATION: /note= "Xaa is an unknown amino acid"

(xi) SEQUENCE DESCRIPTION: SEQ ID NO: 43:

Ala Met Gly Asp Lys Pro Gly Pro Xaa Ile Thr Ala Val Tyr
1               5                   10

(2) INFORMATION FOR SEQ ID NO: 44:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 44:

Ile Ala Lys Val Pro Pro Gly Pro Asn Ile Thr Ala Glu Tyr Gly Asp
1               5                   10                  15

Lys Trp Leu Asp Ala Lys Ser Thr Trp Tyr Gly Lys Pro Thr
            20                  25                  30

(2) INFORMATION FOR SEQ ID NO: 45:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 15-16
        (D) OTHER INFORMATION: /note= "Xaa is an unknown amino acid"

(xi) SEQUENCE DESCRIPTION: SEQ ID NO: 45:

Ala Ile Gly Asp Lys Pro Gly Pro Lys Ile Thr Ala Thr Tyr Xaa Xaa
1               5                   10                  15

Lys Trp Leu Glu Ala Lys Ala Thr
            20

(2) INFORMATION FOR SEQ ID NO: 46:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 46:

AACAATGGC                                                                    9
```

(2) INFORMATION FOR SEQ ID NO: 47:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 9
        (D) OTHER INFORMATION: /note= "Xaa is an unknown amino acid"

(xi) SEQUENCE DESCRIPTION: SEQ ID NO: 47:

```
Ala Met Gly Asp Lys Pro Gly Pro Xaa Ile Thr Ala Thr Tyr Gly Asp
1               5                   10                  15

Lys Trp Leu Asp Ala Lys Ala Thr Phe Tyr Gly
            20                  25
```

(2) INFORMATION FOR SEQ ID NO: 48:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 9
        (D) OTHER INFORMATION: /note= "Xaa is an unknown amino acid"

(ix) FEATURE:
        (A) NAME/KEY: Modified-site
        (B) LOCATION: 18
        (D) OTHER INFORMATION: /note= "Xaa is an unknown amino acid"

(xi) SEQUENCE DESCRIPTION: SEQ ID NO: 48:

```
Ala Ile Gly Asp Lys Pro Gly Pro Xaa Ile Thr Ala Thr Tyr Gly Ser
1               5                   10                  15

Lys Xaa Leu Glu Ala Lys Ala Thr Phe Tyr
            20                  25
```

(2) INFORMATION FOR SEQ ID NO: 49:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 9
        (D) OTHER INFORMATION: /note= "Xaa is an unknown amino acid"

(xi) SEQUENCE DESCRIPTION: SEQ ID NO: 49:

```
Ala Met Gly Asp Lys Pro Gly Pro Xaa Ile Thr Ala Val Tyr
1               5                   10
```

(2) INFORMATION FOR SEQ ID NO: 50:

```
    (i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 50:

Ala Ile Gly Asp Lys Pro
1               5

(2) INFORMATION FOR SEQ ID NO: 51:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 2
        (D) OTHER INFORMATION: /note= "Xaa could be either Ile or Met"

(xi) SEQUENCE DESCRIPTION: SEQ ID NO: 51:

Ala Xaa Gly Asp Lys Pro Gly Pro
1               5

(2) INFORMATION FOR SEQ ID NO: 52:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 52:

Asn Tyr Leu Ala Leu Leu Val Lys Tyr Ala
1               5                   10
```

PROTEIN ALLERGENS OF THE SPECIES *CYNODON DACTYLON*

This application is a divisional of U.S. Ser. No. 07/969,875, filed on Oct. 30, 1992, now abandoned and which is hereby incorporated herein by reference.

BACKGROUND OF THE INVENTION

Bermuda grass (*Cynodon dactylon*) is an important source of pollen allergens in many areas of the world, especially in tropical and sub-tropical climates. These allergens have been studied by a number of means including IgE immunoblotting (Ford D., and Baldo, B. A. *J. Allergy Clin. Immunol.* 79: 711–720 (1987); Shen H. D., et al., *Clin. Allergy* 18: 401–409 (1988), column chromatography (Orren, A., and Dowdle, *S. Afr. Med. J.* 51: 586 (1977); Matthiesen et al., *J. Allergy Clin. Immunol.* 81: 266 (Ab) (1988)), and immuno-electrophoresis (Matthiesen et al., supra, 1988).

The major allergen of Bermuda grass pollen allergen has been identified as a protein with a molecular weight (MW) in the range of 30–34 kD, binding IgE from sera of more than 76% of individuals allergic to Bermuda grass (Ford and Baldo, (1987) Supra; Shen et al, (1988) Supra, and has been designated Cyn d I (Kahn and Marsh, (1986) *Mol. Immunol.*, 23:1281–1288; Marsh et al., (1988) *Ann. Allergy*, 60:499–504, Matthiesen et al, 1988, Supra). Cyn d I is a member of the Group I family of allergens (Kahn and Marsh, (1986) Supra, found in many taxonomically related grasses including ryegrass (Lol p I), Kentucky bluegrass (Poa p I) and Timothy grass (Phl p I) (Standring et al, 1987 *Int. Archs Allergy Appl. Immun.*, 83, 96–103; Esch and Klapper, (1987) *J. Allergy Clin. Immunol.*, 79:489–495; Matthiesen and Lowenstein (1991) *Clin. Exp. Allergy*, 21, 309–320. However, the allergens of Bermuda grass show limited antibody cross-reactivity with those of other grasses (March et al., Supra, Berstein et al. (1976) *J. Allergy Clin. Immunol.*, 57:141–152. A number of studies have shown that Cyn d I differs from the Group I homologues of closely related grasses (Matthiesen and Lowenstein, (1991) Supra. The sequence of the first 27 amino acids at the N-terminus of Cyn d I has been determined. (Matthiesen et al, 1988, Supra; Matthiesen et al, (1990) *Epitopes of Atopic Allergens*, Brussels, UCB Institute of Allergy, 9–13; Singh et al, *Monographs in Allergy*, (1990), 28:101–120; Matthiesen and Lowenstein, (1991), supra).

The presence of Bermuda grass pollen allergens in the environment causes hayfever and seasonal asthma in many individuals and continues to have significant socioeconomic impact on Western communities. While the available spectrum of drugs, including anti-histamines and steroids, have resulted in improvement in the treatment of allergic disease, they do have unfortunate side-effects associated with long term usage. Because of these problems, renewed interest has been shown in the immunotherapy of allergic disease. Immunotherapy involves the injection of potent allergen extracts to desensitize patients against allergic reactions (Bousquet, J. and Michel, F. B., (1989) *Allergy and Clin Immol. News* 1: 7–10. Unfortunately, the pollen preparations used as allergens are polyvalent and of poor quality. Consequently, crude extracts are frequently used at high concentrations and may trigger potentially lethal systemic reactions, including anaphylaxis. The product expressed from the cloned gene, fragments thereof, or synthetic peptides based on the sequence of the allergens provide a safer medium for therapy since they can be quality controlled, characterized and standardized, and they optimally do not bind IgE.

SUMMARY OF THE INVENTION

The present invention provides nucleic acid sequences coding for the major protein allergen of the species *Cynodon dactylon* (Cyn d I), or at least one fragment thereof or the functional equivalent of such nucleic acid sequences. The present invention also provides expression vectors comprising such nucleic acid sequences and host cells transformed therewith. The present invention further provides isolated recombinantly, chemically or synthetically produced Cyn d I or fragments thereof. Isolated Cyn d I or antigenic fragments thereof are useful for diagnosing and treating sensitivity in an individual to Bermuda grass pollen allergens.

BRIEF DESCRIPTION OF THE FIGURES

FIG. 1 shows the nucleotide sequence (SEQ ID NO: 1) coding for and educed partial amino acid sequence (SEQ ID NO: 2) of Cyn d I derived from a cDNA clone designated clone 2 (C2).

FIG. 2 shows a partial nucleotide sequence (SEQ ID NO: 3) coding for and deduced partial amino acid sequence (SEQ ID NO: 4) of Cyn d I, derived from a cDNA clone designated clone 18 (C18).

FIG. 3 shows a comparison of the nucleic acid sequences of clones 2 (SEQ ID NO: 1) and 18 (SEQ ID NO: 3).

FIG. 4 shows a comparison of the deduced amino acid sequences of clones 2 (SEQ ID NO: 2) and 18 (SEQ ID NO: 4).

FIG. 5 shows a comparison of the deduced amino acid sequences of seven clones coding for Cyn d I; clone 18, (C18) (SEQ ID NO: 4), clone 22 (C22) (SEQ ID NO: 5), clone 23 (C23) (SEQ ID NO: 5), clone 2 (C2) (SEQ ID NO: 2), clone 3 (C3) (SEQ ID NO: 7), clone 21 (C21) (SEQ ID NO: 8), and clone 33 (C33) (SEQ ID NO: 9);

FIG. 6 shows a partial nucleotide sequence (SEQ ID NO: 10) coding for and deduced partial amino acid sequence (SEQ ID NO: 11) of Cyn d I derived from a cDNA clone designated clone 14a1.

FIG. 7 shows the partial nucleotide sequence (SEQ ID NO: 12) coding for partial and deduced partial amino acid sequence (SEQ ID NO: 13) of Cyn d I derived from a cDNA clone designated clone 14c1.

FIG. 8 shows a partial amino acid sequence (SEQ ID NO: 14) of Cyn d I designated Cyn d I.14 predicted from a composite of clones 14a1 and 14c1.

FIG. 9 shows a predicted full-length amino acid sequence (SEQ ID NO: 15) of Cyn d I designated Cyn d I.18.

FIG. 10 shows a predicted partial amino acid (SEQ ID NO: 16) sequence of Cyn d I designated Cyn d I.2/3.

FIG. 15 shows a partial nucleotide sequence (SEQ ID NO: 17) coding for and deduced partial amino acid sequence (SEQ ID NO: 7) of Cyn d I derived from a cDNA clone designated clone 3.

FIG. 16 shows a partial nucleotide sequence (SEQ ID NO: 18) coding for and deduced partial amino acid sequence (SEQ ID NO: 5) of Cyn d I derived from a cDNA clone designated clone 22.

FIG. 17 shows a partial nucleotide sequence (SEQ ID NO: 19) coding for and deduced partial amino acid (SEQ ID NO: 5) sequence of Cyn d I derived from a cDNA clone designated clone 23.

FIG. 18 shows a nucleotide sequence (SEQ ID NO: 20) and deduced amino acid sequence (SEQ ID NO: 21) of Cyn d I derived from a full-length cDNA clone designated CD1.

FIG. 19 shows a partial nucleotide sequence (SEQ ID NO: 22) and deduced amino acid sequence (SEQ ID NO: 23) of Cyn d I derived from a cDNA clone designated KAT-39-1.

FIG. 20 shows the comparison of predicted full-length amino acid sequences of the Cyn d I mature proteins designated Cyn d I.18 (SEQ ID NO: 15), Cyn d I.CD1 (SEQ ID NO: 21) and Cyn d I.2/3 (full-length) (SEQ ID NO: 24).

DETAILED DESCRIPTION OF THE INVENTION

Figure 11A:
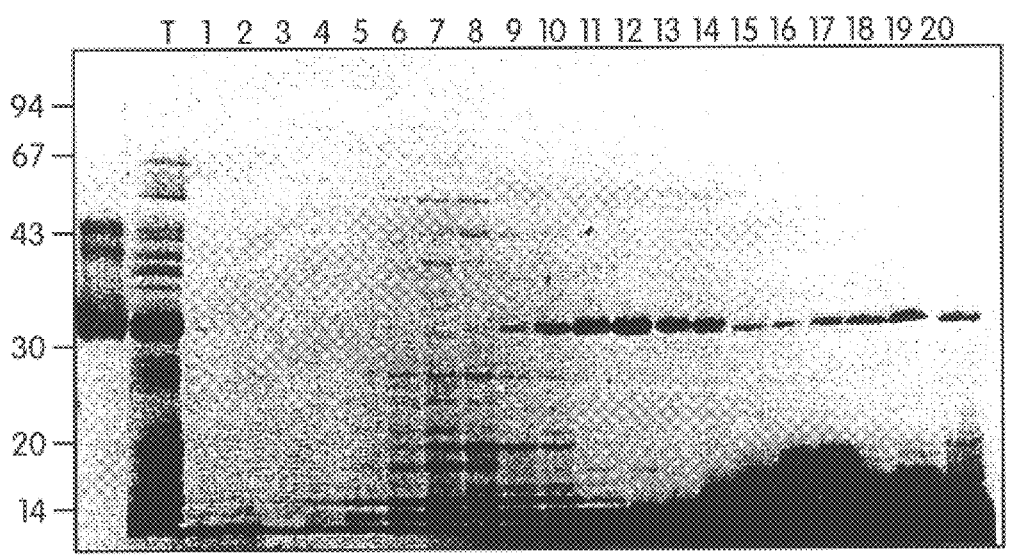
FIG. 11*a* shows separation by SDS-PAGE of protein fractions obtained by the primary preparative isoelectric focusing (IEF) of these proteins on the Rotofor.

The present invention provides nucleic acid sequences, or the functional equivalents thereof, coding for Cyn d I, the major allergen found in Bermuda grass pollen. Cyn d I appears to be a family of closely related allergens. As defined herein, a "family of allergens" are proteins related in function and amino acid sequence but encoded by genes at separate genetic loci. Each family member can have polymorphism in which nucleotide variation may occur at a given genetic loci. Polymorphism in the nucleic acid sequence may result in amino acid polymorphism, but this is not always the case as the nucleotide code which encodes for the amino acids is degenerate. The nucleic acid sequence coding for Cyn d I, may vary among individual Bermuda grass plants due to natural allelic variation. Any and all such nucleotide variations and resulting amino acid polymorphisms are within the scope of the invention.

A partial nucleic acid sequence coding for Cyn d I, derived from a cDNA clone designated clone 2, has the sequence shown in FIG. 1 (SEQ ID NOs: 1 and 2). The partial nucleic acid sequence (SEQ ID NO: 1) coding for Cyn d I shown in FIG. 1 comprises 435 bases. The 3' untranslated region starts at base 436 and extends to base 662. The deduced partial amino acid (SEQ ID NO: 2) sequence of Cyn d I encoded for by clone 2 (C2) is also shown in FIG. 1.

FIG. 2 shows the partial nucleic acid (SEQ ID NO: 3) and deduced amino acid sequences (SEQ ID NO: 4) for a second cDNA clone designated clone 18 (C18). The nucleic acid sequence (SEQ ID NO: 3) coding for Cyn d I shown in FIG. 2 comprises 600 nucleotides encoding 200 deduced amino acids. The 3' untranslated region starts at base 601 and extends to base 775.

As shown in FIG. 3, although the coding sequences for clone 2 (SEQ ID NO: 1) and clone 18 (SEQ ID NO: 3) are clearly homologous, the 3' untranslated regions are much more divergent. This suggests that clones 2 and 18 may encode separate members of a Cyn d I gene family.

As shown in FIG. 4, the deduced amino acid sequences encoded by clone 2 (SEQ ID NO: 2) and clone 18 (SEQ ID NO: 4) have 88.2% homology (84.1% identity). There are 22 amino acid differences in the 143 amino acid overlap deduced from the two clones of which 6 are conservative substitutions and 16 are non-conservative substitutions. The partial protein encoded by clone 18 (SEQ ID NO: 4) is two amino acids longer at the carboxy terminus than the partial protein encoded by clone 2 (FIG. 4) (SEQ ID NO: 2). Amino acid homology was demonstrated using software contained in PCGENE (Intelligenetics, Mountain View, Calif.).

A comparison of the deduced amino acid sequences encoded by seven cDNA clones derived from the Cyn d I library as described in Example I are shown in FIG. 5 (SEQ ID NOs: 2, and 4–9). The amino acid sequences encoded by these cDNA clones designated C2 (SEQ ID NO: 2), C3 (SEQ ID NO: 7) C21 (SEQ ID NO: 8), C22 (SEQ ID NO: 5), C23 (SEQ ID NO: 5) and C33 (SEQ ID NO: 9) are shown aligned with the deduced amino acid sequence encoded by clone 18 (C18) (SEQ ID NO: 4), which is the longest clone derived from the Cyn d I cDNA library. As is shown in FIG. 5 and FIG. 6, the overlapping portion of the amino acid sequences encoded by clones 18 (SEQ ID NO: 4), 22 (SEQ ID NO: 5), 23 (SEQ ID NO: 5), 21 (SEQ ID NO: 8) and 33 (SEQ ID NO: 9) are identical. This suggests that clones 18 (SEQ ID NO: 4), 22 (SEQ ID NO: 5), 23 (SEQ ID NO: 5), 21 (SEQ ID NO: 8) and 33 (SEQ ID NO: 9) are examples of the same Cyn d I gene family member. However, clones 22 and 23 are two amino acids shorter than clone 18 and have different 3' untranslated regions (FIGS. 2, 16 and 17). This may suggest that clones 22 and 23 represent a separate member of the Cyn d I gene family. Alternatively, they could represent differentially spliced forms of the same family member.

As is shown in FIG. 5, there are only five amino acid differences between the deduced amino acid sequences encoded by clones 2 (SEQ ID NO: 2) and 3 (SEQ ID NO: 7). Accordingly, clones 2 and 3 may represent polymorphisms of a Cyn d I gene family member, which Cyn d I gene family member is different from the Cyn d I gene family member(s) to which clones 18 (SEQ ID NO: 4), 21 (SEQ ID NO: 8), and 33 (SEQ ID NO: 9) belong. Assuming that clones 2 (SEQ ID NO: 2) and 3 (SEQ ID NO: 7) do represent polymorphisms of a Cyn d I gene family member, a predicted partial amino acid sequence of Cyn d I designated Cyn d I.2/3 (SEQ ID NO: 16) as shown in FIG. 10 may be generated from the amino acid sequences encoded by clones 2 (SEQ ID NO: 2) and 3 (SEQ ID NO: 7).

FIG. 6 shows the nucleotide sequence of cDNA clone 14a1 (SEQ ID NO: 10) and its deduced amino acid sequence (SEQ ID NO: 11). This clone was isolated from a PCR as described in Example 2 and the amino acid sequence it encodes corresponds to the amino portion of the Cyn d I family member partially encoded by clone 18 (SEQ ID NO: 4). There is a 19 nucleotide overlap between the 3' end of clone 14a1 (SEQ ID NO: 10) and the 5' end of clone 18. Clone 14a1 (SEQ ID NO: 10) was amplified in the PCR using oligonucleotide primers based on non-coding strand sequence of clone 18, as described in Example 2. The methionine encoded by nucleotides 41–43 of clone 14a1 (SEQ ID NO: 10) presumably represents the first amino acid of the translated protein. This is the first methionine encoded after the in-frame stop codon at nucleotides 11–13 of clone 14a1 (SEQ ID NO: 10) indicating that the initiation of protein translation does not occur 5' of the methionine encoded by nucleotides 41–43 of clone 14a1 (SEQ ID NO:10). The nucleotide sequence surrounding the presumptive initiator methionine has a 78% match with the consensus sequence, 5' AACAATGGC-3' (SEQ ID NO: 46) (Lutcke et al. 1987. *EMBO J.* 6:43–48), for protein initiation in plants. There is a leader sequence of 22 amino acids before the start of the N-terminus of the mature Cyn d I protein (indicated by amino acid 1 in FIG. 6) (SEQ ID NO: 11), the N-terminus of the mature Cyn d I protein (the first 27 amino acids) having previously been identified (Matthiesen et al., 1988, *J. Allergy Clin. Immunol.* 81:226; Singh et al., 1990, *Monogr. Allergy,* 28:101–120; Matthiesen et al., 1991, *J. Allergy Clin. Immunol.,* 88:763–774).

FIG. 7 shows the nucleotide sequence of cDNA clone 14c1 (SEQ ID NO: 12) and its deduced amino acid sequence (SEQ ID NO: 13). This clone was also isolated from a PCR as described in Example 2 and the amino acid sequence (SEQ ID NO: 13) it encodes corresponds to the amino portion of the Cyn d I family member partially encoded by clone 18 (SEQ ID NO: 4). This clone is homologous with clone 14a1 (SEQ ID NO: 11), but has one amino acid difference with clone 14a1 in the sequence of the mature protein (the N-terminus of the mature Cyn d I protein being indicated by amino acid 1 in FIG. 7) (SEQ ID NO: 13). Clone 14c1 (SEQ ID NOs: 12 and 13) as nucleotide differences in the leader sequence encoding seven amino acid differences with clone 14a1 (SEQ ID NO: 11), including a 12 nucleotide insert that would encode an additional 4 amino acids. A composite sequence of 14a1 and 14c1 including the potential polymorphisms of these clones is designated Cyn d 1.14 (SEQ ID NO: 14) shown in FIG. 8.

The sequences of clones 14a1 (SEQ ID NO: 11) and 14c1 (SEQ ID NO: 13) are useful in generating a predicted full-length nucleic acid sequence encoding Cyn d I. Predicted full-length nucleotide sequences encoding Cyn d I may be derived from the formula:

$$L_1NYX$$

wherein $L_1$ is a nucleic acid sequence of 0–300 nucleotides which includes nucleotides which encode a leader sequence of the Cyn d I protein and which may also include nucleotides of a 5' untranslated region, N is a nucleic acid sequence comprising up to 600 nucleotides and includes nucleotides which encode the amino terminus portion of mature Cyn d I, Y is that portion of the nucleic acid sequence of clone 2 (SEQ ID NO: 1), clone 18 (SEQ ID NO: 3), clone 3 (SEQ ID NO: 17), clone 22 (SEQ ID NO: 18), or clone 23 (SEQ ID NO: 19) or any polymorphic form of those clones which encodes the mature Cyn d I protein and X is a nucleic acid sequence of 0–600 nucleotides which includes nucleotides of the 3' untranslated portion of Cyn d I. For example, $L_1$ may include the nucleic acid sequence represented by nucleotides 1–106 of clone 14a1 (SEQ ID NO: 10) as shown in FIG. 6 which includes the 5' untranslated region of clone 14a1 as well as those nucleotides (nucleotides 41–106 as shown in FIG. 6) of clone 14a1 which encode a Cyn d I leader sequence. $L_1$ may also include the nucleic acid sequence represented by nucleotides 1–103 of clone 14c1 (SEQ ID NO: 12) as shown in FIG. 7 which includes the 5' untranslated region of clone 14c1 as well as those nucleotides (nucleotides 28–103 as shown in FIG. 7) of clone 14c1 which encode a Cyn d I leader sequence. $L_1$ may also be a nucleic acid sequence which includes nucleotides of clone 14a1 which encode only the leader sequence portion of Cyn d I (nucleotides 41–106 as shown in FIG. 6) (SEQ ID NO: 10) or the nucleotides of clone 14c1 which encode only the leader sequence portion of Cyn d I (nucleotides 28–103 as shown in FIG. 7) (SEQ ID NO: 12) or any polymorphic form thereof. When one is generating a nucleic acid sequence encoding mature Cyn d I, then $L_1$ is 0 and X is 0 and the formula then simply is NY. N is preferably the nucleic acid sequence represented by nucleotides 107–244 of clone 14a1 (SEQ ID NO: 10) as shown in FIG. 6 or nucleotides 104–243 of clone 14c1 (SEQ ID NO: 12) as shown in FIG. 7, each sequence of which encodes the amino terminus of mature Cyn d I does not overlap the nucleic acid sequence of Y. Y is preferably that portion of the nucleic acid sequence of clone 2 (SEQ ID NO: 1), clone 18 (SEQ ID NO: 3), clone 3 (SEQ ID NO: 17), clone 22 (SEQ ID NO: 18), or clone 23 (SEQ ID NO: 19) which encodes the mature Cyn d I protein and does not represent 3' untranslated region. For example Y may include nucleotides 1–603 of clone 18 (SEQ ID NO: 3) as shown in FIG. 2, nucleotides 1–594 of clone 22 (SEQ ID NO: 18) as shown in FIG. 16, or nucleotides 1–595 of clone 23 (SEQ ID NO: 19) as shown in FIG. 17. Y may also include nucleotides 1–438 of clone 2 (SEQ ID NO: 1) as shown in FIG. 1, or nucleotides 1–417 of clone 3 (SEQ ID NO: 17) as shown in FIG. 15. X is preferably a nucleic acid sequence which includes nucleotides of the 3' untranslated portion of clones 2 (SEQ ID NO: 1), 3 (SEQ ID NO: 17), 18 (SEQ ID NO: 3), 22 (SEQ ID NO: 18), or 23 (SEQ ID NO: 19). For example, X may include nucleotides 604–775 of clone 18 (SEQ ID NO: 3) as shown in FIG. 2, nucleotides 595–802 of clone 22 (SEQ ID NO: 18) as shown in FIG. 16, nucleotides 596–832 of clone 23 (SEQ ID NO: 19) as shown in FIG. 15, nucleotides 439–662 of clone 2 (SEQ ID NO: 1) as shown in FIG. 1 or nucleotides 418–594 of clone 3 (SEQ ID NO: 17) as shown in FIG. 15. As discussed previously, X is 0 when one is generating a nucleic acid sequence encoding mature Cyn d I. Specific examples of composite amino acid sequences of Cyn d I generated from the above-described formula include but are not limited to the following composite sequences: the nucleic acid sequence of $L_1$ includes nucleotides 1–106 of clone 14a1 (SEQ ID NO: 10) as shown in FIG. 6 or nucleotides 1–103 of clone 14c1 (SEQ ID NO: 12) as shown in FIG. 7, the sequence of N is represented by nucleotides 107–244 of clone 14a1 (SEQ ID NO: 10) or nucleotides 104–243 of clone 14c1 (SEQ ID NO: 12) as shown in FIG. 7. The nucleic acid sequence of Y includes nucleotides 1–603 of clone 18 (SEQ ID NO: 3) as shown in FIG. 2 and the nucleic acid sequence of X includes nucleotides 604–775 of clone 18 (SEQ ID NO: 3) as shown in FIG. 2.

Other predicted composites of full-length amino acid sequences of Cyn d I may be derived from the nucleic acid sequences of the above formula which encodes the full-length or mature Cyn d I protein.

A predicted full-length amino acid sequence for Cyn d I designated Cyn d I.18 (SEQ ID NO: 15) shown in FIG. 9 can be generated by merging the amino acid sequence shown in FIG. 8 designated Cyn d I.14 (SEQ ID NO: 14) with amino acid residues 53–246 of clone 18 (SEQ ID NO: 4) as shown in FIG. 5. The predicted composite of the mature protein in this case, which comprises amino acid 1–246 of Cyn d I.18 (SEQ ID NO: 15) shown in FIG. 9 would have a predicted molecular weight of approximately 26.7 kDa without any post-translational modifications. As used herein, the "mature" Cyn d I protein does not include the amino acid sequence of the leader portion of the Cyn d I protein. In all applicable figures discussed herein, polymorphism or potential polymorphism is shown in superscript and subscript.

A full-length clone was generated using PCR as discussed in Example 3 and as shown in FIGS. 18 and 20 (SEQ ID NOs: 20 and 21). The full-length clone shown in FIG. 18 and designated clone CD1 was generated from a PCR using oligonucleotide primers based on nucleotides 107–125 of clone 14a1 (SEQ ID NO: 10) (FIG. 6) and nucleotides 604–621 of clone 18 (SEQ ID NO: 3) (FIG. 2). The deduced amino acid sequence of clone CD1 (SEQ ID NO: 21) corresponds to the predicted composite full-length amino acid sequence of the Cyn d I protein family member designated Cyn d I.18 (SEQ ID NO: 15), as discussed above and as shown in FIG. 9, with the exception of two amino acids. The deduced amino acid sequence of clone CD1 (SEQ ID NO: 21) as shown in FIGS. 18 and 20 is designated Cyn d I.CD1. Cyn d I.CD1 is substantially the same Cyn d I protein as the predicted composite sequence represented by Cyn d I.18 (SEQ ID NO: 15) shown in FIG. 9. A host cell transformed with a vector comprising the cDNA insert of clone CD1 (SEQ ID NO: 20) has been deposited with the ATCC under accession number 69107.

Another predicted composite full-length amino acid sequence designated Cyn d I.2/3 (full-length) (SEQ ID NO: 24) is shown in FIG. 20. Part of this sequence is deduced from a Cyn d I clone which was generated from a PCR using oligonucleotide primers based on nucleotides 178–206 of clone 2 (SEQ ID NO: 1) (FIG. 1) (which is identical to the corresponding nucleotide sequence of clone 3 (SEQ ID NO: 17) (FIG. 15)) and nucleotides essentially identical to nucleotides 107–130 of clone 14a1 (SEQ ID NO: 10) (FIG. 6). This clone was designated clone KAT-39-1. The nucleotide (SEQ ID NO: 22) and deduced amino acid sequences (SEQ ID NO: 23) of clone KAT-39-1 are shown in FIG. 19. The deduced amino acid sequence of clone KAT-39-1 (SEQ ID NO: 23) represents a partial amino acid sequence of Cyn d I that overlaps with part of the predicted amino acid sequence of Cyn d I.2/3 (SEQ ID NO: 16) as shown in FIG. 10. Therefore, the composite sequence formed by combining the nucleic and deduced amino acid sequences of clone KAT-39-1 in conjunction with the nucleic and deduced amino acid sequences of Cyn d I.2/3 represent the nucleic and deduced amino acid sequences of the predicted Cyn d I protein family member composite designated Cyn d I.2/3 (full-length) (SEQ ID NO: 24) as shown in FIG. 20. FIG. 20 shows a comparison of the amino acid sequences of composite sequences designated Cyn d I.18 (SEQ ID NO: 15) and Cyn d I.2/3 (full-length) (SEQ ID NO: 24), and the full-length amino acid sequence deduced from the full-length cDNA clone, CD1, designated Cyn d I.CD1 (SEQ ID NO: 21).

Nucleic acids encoding Cyn d I protein allergens as described above may be obtained from any part of *Cynodon dactylon* plants. Nucleic acids encoding Cyn d I may be obtained from genomic DNA. The nucleic acids coding for Cyn d I may be obtained using the methods disclosed herein or any other suitable technique for isolation and cloning of genes.

Fragments of the nucleic acid sequence coding for fragments of Cyn d I are also within the scope of the invention. Fragments within the scope of the invention include those coding for parts of Cyn d I which induce an immune response in mammals, preferably humans, such as stimulation of minimal amounts of IgE; binding of IgE; eliciting the production of IgG and IgM antibodies; or the eliciting of a T cell response such as proliferation and/or lymphokine secretion and/or the induction of T cell anergy. The foregoing fragments of Cyn d I are referred to herein as antigenic fragments. Fragments within the scope of the invention also include those capable of hybridizing with nucleic acid from other plant species for use in screening protocols to detect allergens that are cross-reactive with Cyn d I. As used herein, a fragment of the nucleic acid sequence coding for Cyn d I refers to a nucleotide sequence having fewer bases than the nucleotide sequence coding for the entire amino acid sequence of Cyn d I and/or mature Cyn d I. Generally, the nucleic acid sequence coding for the fragment or fragments of Cyn d I will be selected from the bases coding for the mature protein, however, in some instances it may be desirable to select all or a part of a fragment or fragments from the leader sequence portion of the nucleic acid sequence of the invention. The nucleic acid sequence of the invention may also contain linker sequences, modified restriction endonuclease sites and other sequences useful for cloning, expression or purification of Cyn d I or fragments thereof.

The present invention provides expression vectors and host cells transformed to express the nucleic acid sequences of the invention. Nucleic acid coding for Cyn d I, or at least one fragment thereof may be expressed in bacterial cells such as *E. coli,* insect cells (baculovirus), yeast, or mammalian cells such as Chinese hamster ovary cells (CHO). Suitable expression vectors, promoters, enhancers, and other expression control elements may be found in Sambrook et al. *Molecular Cloning: A Laboratory Manual,* second edition, Cold Spring Harbor Laboratory Press, Cold Spring Harbor, N.Y. (1989). Other suitable expression vectors, promoters, enhancers, and other expression elements are known to those skilled in the art. Expression in mammalian, yeast or insect cells leads to partial or complete glycosylation of the recombinant material and formation of any inter- or intra-chain disulfide bonds. Suitable vectors for expression in yeast include YepSec1 (Baldari et al. (1987) *Embo J.* 6: 229–234); pMFa (Kurjan and Herskowitz (1982) *Cell* 30: 933–943); JRY88 (Schultz et al. (1987) *Gene* 54: 113–123) and pYES2 (Invitrogen Corporation, San Diego, Calif.). These vectors are freely available. Baculovirus and mammalian expression systems are also available. For example, a baculovirus system is commercially available (PharMingen, San Diego, Calif.) for expression in insect cells while the pMSG vector is commercially available (Pharmacia, Piscataway, N.J.) for expression in mammalian cells.

For expression in *E. coli,* suitable expression vectors include, among others, pTRC (Amann et al. (1988) *Gene* 69: 301–315); pGEX (Amrad Corp., Melbourne, Australia); pMAL (N.E. Biolabs, Beverly, Mass.); pRIT5 (Pharmacia, Piscataway, N.J.); pET-11d (Novagen, Madison, Wis.) Jameel et al., (1990) *J. Virol.* 64:3963–3966; and pSEM (Knapp et al. (1990) *BioTechniques* 8: 280–281). The use of pTRC, and pET-11d, for example, will lead to the expression of unfused protein. The use of pMAL, pRIT5 pSEM and pGEX will lead to the expression of allergen fused to maltose E binding protein (pMAL), protein A (pRIT5), truncated β-galactosidase (PSEM), or glutathione S-transferase (pGEX). When Cyn d I, fragment, or fragments thereof is expressed as a fusion protein, it is particularly advantageous to introduce an enzymatic cleavage site at the fusion junction between the carrier protein and Cyn d I or fragment thereof. Cyn d I or a fragment thereof may then be recovered from the fusion protein through enzymatic cleavage at the enzymatic site and biochemical purification using conventional techniques for purification of proteins and peptides. Suitable enzymatic cleavage sites include those for blood clotting Factor Xa or thrombin for which the appropriate enzymes and protocols for cleavage are commercially available from, for example, Sigma Chemical Company, St. Louis, Mo. and N.E. Biolabs, Beverly, Mass.. The different vectors also have different promoter regions allowing constitutive or inducible expression with, for example, IPTG induction (PRTC, Amann et al., (1988) supra; pET-11d, Novagen, Madison, Wis.) or temperature induction (pRIT5, Pharmacia, Piscataway, N.J.). It may also be appropriate to express recombinant Cyn d I in different *E. coli* hosts that have an altered capacity to degrade recombinantly expressed proteins (e.g. U.S. Pat. No. 4,758,512). Alternatively, it may be advantageous to alter the nucleic acid sequence to use codons preferentially utilized by *E. coli*, where such nucleic acid alteration would not affect the amino acid sequence of the expressed protein.

Host cells can be transformed to express the nucleic acid sequences of the invention using conventional techniques such as calcium phosphate or calcium chloride co-precipitation, DEAE-dextran-mediated transfection, or electroporation. Suitable methods for transforming the host cells may be found in Sambrook et al. supra, and other laboratory textbooks. The nucleic acid sequences of the invention may also be synthesized using standard techniques.

The present invention also provides a method of producing purified Cyn d I or at least one fragment thereof comprising the steps of culturing a host cell transformed with a DNA sequence encoding Cyn d I or at least one fragment thereof in an appropriate medium to produce a mixture of cells and medium containing Cyn d I or at least one fragment thereof; and purifying the mixture to produce substantially pure Cyn d I or at least one fragment thereof. Host cells transformed with an expression vector containing DNA coding for Cyn d I or at least one fragment thereof are cultured in a suitable medium for the host cell. Cyn d I protein and peptides can be purified from cell culture medium, host cells, or both using techniques known in the art for purifying peptides and proteins including ion-exchange chromatography, gel filtration chromatography, ultrafiltration, electrophoresis and immunopurification with antibodies specific for Cyn d I or fragments thereof. The terms isolated and purified are used interchangeably herein and refer to peptides, protein, protein fragments, and nucleic acid sequences substantially free of cellular material or culture medium when produced by recombinant DNA techniques, or chemical precursors or other chemicals when synthesized chemically. Accordingly, an isolated peptide of the invention is produced by recombinant DNA techniques or synthesized chemically and is substantially free of cellular material, culture medium, chemical precursors or other chemicals.

Another aspect of the invention provides preparations comprising Cyn d I or at least one fragment thereof synthesized in a host cell transformed with a DNA sequence encoding all or a portion of Cyn d I, or chemically synthesized, and purified Cyn d I protein, or at least one antigenic fragment thereof produced in a host cell transformed with a nucleic acid sequence of the invention, or chemically synthesized. In preferred embodiments of the invention, the Cyn d I protein is produced in a host cell transformed with the nucleic acid sequence coding for at least the mature Cyn d I protein.

Fragments of Cyn d I can be obtained, for example, by screening peptides synthesized from the corresponding fragment of a nucleic acid sequence of the invention coding for such peptides or synthesized chemically using techniques known in the art. Peptide fragments of the allergen may be obtained by selection of fragments of a desired length with no overlap of the peptides, or selection of overlapping fragments of a desired length, which can be produced recombinantly or synthetically. The fragments can be tested to determine antigenicity (e.g., the ability of the fragment to induce an immune response). Such fragments are referred to herein as antigenic fragments. Fragments of Cyn d I protein allergen which are capable of eliciting a T cell response such as stimulation (i.e., proliferation or lymphokine secretion) and/or are capable of inducing T cell anergy are particularly desirable. Fragments of Cyn d I which do not bind immunoglobulin E (IgE) or bind IgE to a substantially lesser extent than the protein allergen from which the fragments are derived are also particularly desirable. The major complications of standard immunotherapy are systemic responses such as anaphylaxis. Immunoglobulin E is a mediator of anaphylactic reactions which result from the binding and cross-linking of antigen to IgE on mast cells or basophils and the release of mediators (e.g., histamine, serotonin, eosinophil, chemotactic factors). Thus, anaphylaxis could be avoided by the use of a fragment which does not bind IgE, or if the fragment binds IgE, such binding does not result in the release of mediators (e.g., histamine etc.) from mast cells or basophils. In addition, fragments which have minimal IgE stimulating activity are particularly desirable for therapeutic effectiveness. Minimal IgE stimulating activity refers to IgE stimulating activity which is less than the amount of IgE production stimulated by the whole Bermuda grass protein allergen. Preferred fragments of the invention include but are not limited to fragments derived from amino acids 5-246, 10-246, 20-246 and 25-246 of Cyn d I.18 (SEQ ID NO: 15) as shown in FIG. 20; fragments derived from amino acids 5-246, 10-246, 20-246 and 25-246 of Cyn d I.CD1 (SEQ ID NO: 21) as shown in FIG. 20; and fragments derived from amino acids 5-244, 10-244, 20-244 and 25-244 of Cyn d I.2/3 (full-length) (SEQ ID NO: 24) as shown in FIG. 20.

Cyn d I and preferred antigenic fragments thereof, when administered to a Bermuda grass pollen-sensitive individual, are capable of modifying the allergic response of the individual to the allergen, and preferably are capable of modifying the B cell, the T cell response or both the B cell and the T cell response of the individual to the allergen. As used herein, modification of the allergic response of an individual sensitive to a Bermuda grass pollen allergen such as Cyn d I can be defined as non-responsiveness or diminution in symptoms to the allergen, as determined by standard clinical procedures (See e.g., Varney et al., *British Medical Journal* 302: 265–269 (1990)) including diminution in Bermuda grass pollen induced asthmatic symptoms. As referred to herein, a diminution in symptoms includes any reduction in symptoms in the allergic response of an individual to the allergen following a treatment regimen with a protein or peptide of the invention. This diminution in symptoms may be determined subjectively (i.e., the patient feels more comfortable upon exposure to the allergen), or clinically, such as with a standard test. Initial screening for IgE binding to Cyn d I or fragments thereof may be performed by scratch tests or intradermal skin tests on laboratory animals or human volunteers, or in in vitro systems such as RAST (radioallergosorbent test), RAST inhibition, ELISA assay, radioimmunoassay (RIA), or histamine release.

Antigenic fragments of the present invention which have T cell stimulating activity, and comprise at least one T cell epitope are particularly desirable. T cell epitopes are believed to be involved in initiation and perpetuation of the immune response to a protein allergen which is responsible for the clinical symptoms of allergy. These T cell epitopes are thought to trigger early events at the level of the T helper cell by binding to an appropriate HLA molecule on the surface of an antigen presenting cell and stimulating the relevant T cell subpopulation. These events lead to T cell proliferation, lymphokine secretion, local inflammatory reactions, recruitment of additional immune cells to the site, and activation of the B cell cascade leading to production of antibodies. One isotype of these antibodies, IgE, is fundamentally important to the development of allergic symptoms and its production is influenced early in the cascade of events, at the level of the T helper cell, by the nature of the lymphokines secreted. A T cell epitope is the basic element or smallest unit of recognition by a T cell receptor, where the epitope comprises amino acids essential to receptor recognition and may be contiguous and/or non-contiguous in the amino acid sequence of the protein. Amino acid sequences which mimic those of the T cell epitopes and which modify the allergic response to protein allergens are within the scope of this invention.

Exposure of patients to Cyn d I or to the antigenic fragments of the present invention which comprise at least one T cell epitope may tolerize or anergize appropriate T cell subpopulations such that they become unresponsive to the protein allergen and do not participate in stimulating an immune response upon such exposure. In addition, administration of Cyn d I or an antigenic fragment of the present invention which comprises at least one T cell epitope may modify the lymphokine secretion profile as compared with exposure to the naturally-occurring protein allergen or portion thereof (e.g. result in a decrease of IL-4 and/or an increase in IL-2). Furthermore, exposure to Cyn d I or such antigenic fragment may influence T cell subpopulations which normally participate in the response to the allergen such that these T cells are drawn away from the site(s) of normal exposure to the allergen (e.g., nasal mucosa, skin, and lung) towards the site(s) of therapeutic administration of the fragment. This redistribution of T cell subpopulations may ameliorate or reduce the ability of an individual's immune system to stimulate the usual immune response at the site of normal exposure to the allergen, resulting in a dimunution in allergic symptoms.

Cyn d I and fragments or portions derived therefrom (peptides) can be used in methods of diagnosing, treating and preventing allergic reactions to Bermuda grass pollen. Thus, the present invention provides therapeutic compositions comprising isolated Cyn d I or at least one fragment thereof and a pharmaceutically acceptable carrier or diluent. Cyn d I or at least one fragment thereof is preferably produced in a cell transformed to express the protein allergen or the fragment thereof or is synthetically prepared. Administration of the therapeutic compositions of the present invention to an individual to be desensitized can be carried out using known techniques. Cyn d I or a fragment thereof can be administered to an individual in combination with, for example, an appropriate diluent, a carrier and/or an adjuvant. Pharmaceutically acceptable diluents include saline and aqueous buffer solutions. Pharmaceutically acceptable carriers include polyethylene glycol (Wie et al. (1981) Int. Arch. Allergy Appl. Immunol. 64:84–99) and liposomes (Strejan et al. (1984) J. Neuroimmunol. 7: 27). For purposes of inducing T cell anergy, the therapeutic composition is preferably administered in non-immunogenic form, e.g., it does not contain adjuvant. Such compositions will generally be administered by injection (subcutaneous, intravenous etc.), oral administration, inhalation, transdermal application or rectal administration. The therapeutic compositions of the invention are administered to Bermuda grass pollen-sensitive individuals in a treatment regimen at dosages and for lengths of time effective to reduce sensitivity (i.e, reduce the allergic response) of the individual to Bermuda grass pollen. Effective amounts of the therapeutic compositions will vary according to factors such as the degree of sensitivity of the individual to Bermuda grass pollen, the age, sex, and weight of the individual, and the ability of the Bermuda grass pollen allergen or fragment thereof to elicit an antigenic response in the individual.

cDNA coding for a Cyn d I (or the mRNA from which it was transcribed) or a portion thereof can be used to identify similar sequences in any variety or type of plant and thus, to identify or "pull out" sequences which have sufficient homology to hybridize to the cDNA of the protein allergen or mRNA or portion thereof. For example, cDNA of the present invention may hybridize to DNA from temperate grasses such as rye-grass, Kentucky Blue grass, Timothy grass and orchard grass, and from other grasses such as Bahia grass and sorghum, under conditions of low stringency. Those sequences which have sufficient homology (generally greater than 40%) can be selected for further assessment using the method described herein. Alternatively, high stringency conditions can be used. In this manner, DNA of the present invention can be used to identify, in other types of plants, preferably related families, genera, or species, sequences encoding polypeptides having amino acid sequences similar to that of a Cyn d I, and thus to identify allergens in other species. Thus, the present invention includes not only the Bermuda grass allergen Cyn d I, but also other allergens encoded by DNA which hybridizes to DNA of the present invention. The invention further includes isolated protein allergens or fragments thereof, excluding those protein allergens or fragments from the genus Lolium, which are immunologically related to Cyn d I or fragments thereof, such as by antibody cross-reactivity, or other immunological assay wherein the protein allergens or fragments thereof are capable of binding to antibodies specific for Cyn d I or fragments of the invention or by T cell cross-reactivity wherein the isolated allergenic proteins or fragments thereof are capable of stimulating T cells specific for the proteins and peptides of the invention. The invention also includes protein allergens or fragments thereof which have greater than 73% homology with Cyn d I or have greater than 90% homology with Cyn d I.

Proteins or peptides encoded by the cDNA of the present invention can be used, for example as "purified" allergens. Such purified allergens are useful in the standardization of allergen extracts which are key reagents for the diagnosis and treatment of sensitivity to Bermuda grass pollen. Furthermore, by using proteins or fragments thereof based on the nucleic acid sequences of Cyn d I, anti-peptide antisera, polyclonal antibodies or monoclonal antibodies can be made using standard methods. These sera or polyclonal or monoclonal antibodies can be used to standardize allergen extracts and/or used in purification of native or recombinant protein allergens.

Through use of Cyn d I and synthetically or recombinantly produced isolated antigenic fragments thereof, preparations of consistent, well-defined composition and biological activity can be made and administered for therapeutic purposes (e.g. to modify the allergic response of a Bermuda grass pollen-sensitive individual. Administration of such peptides or protein may, for example, modify B-cell response to Cyn d I, T cell response to Cyn d I or both responses. Isolated peptides can also be used to study the mechanism of immunotherapy of Bermuda grass pollen allergy and to design modified derivatives or analogues useful in immunotherapy.

It is possible to modify the structure of Cyn d I or fragments thereof of the invention, for such purposes as increasing solubility, enhancing therapeutic or preventive efficacy, or stability (e.g., shelf life ex vivo, and resistance to proteolytic degradation in vivo). Modified Cyn d I or a modified fragment thereof can be produced in which the amino acid sequence has been altered, such as by amino acid substitution, deletion, or addition, to modify immunogenicity and/or reduce allergenicity, or to which a component has been added for the same purpose. For example, the amino acid residues essential to T cell epitope function can be determined using known techniques (e.g., substitution of each residue and determination of presence or absence of T cell reactivity). Those residues shown to be essential can be modified (e.g., replaced by another amino acid whose presence is shown to enhance T cell reactivity), as can those which are not required for T cell reactivity (e.g., by being replaced by another amino acid whose incorporation enhances T cell reactivity but does not diminish binding to relevant MHC). In order to enhance stability and/or reactivity, Cyn d I or a fragment thereof can also be modified to incorporate one or more polymorphisms in the amino acid sequence of the protein allergen resulting from natural allelic variation. Additionally, D-amino acids, non-natural amino acids or non-amino acid analogues can be substituted or added to produce a modified protein or fragment within the scope of this invention. Furthermore, Cyn d I or fragments thereof can be modified using the polyethylene glycol (PEG) method of A. Sehon and co-workers (Wie et al. supra) to produce a peptide conjugated with PEG. Modifications of Cyn d I or fragments thereof can also include reduction/alkylation (Tarr in: *Methods of Protein Microcharacterization,* J. E. Silver ed. Humana Press, Clifton, N.J., pp 155–194 (1986)); acylation (Tarr, supra); esterification (Tarr, supra); chemical coupling to an appropriate carrier (Mishell and Shiigi, eds, *Selected Methods in Cellular Immunology,* W H Freeman, San Francisco, Calif. (1980); U.S. Pat. No. 4,939,239); or mild formalin treatment (Marsh *International Archives of Allergy and Applied Immunology* 41: 199–215 (1971)).

Site-directed mutagenesis of DNA encoding Cyn d I or fragment thereof can be used to modify the structure. Such methods may involve PCR (Ho et al., Gene 77:51–59 (1989)) or total synthesis of mutated genes (Hostomsky, Z., et al., *Biochem. Biophys. Res. Comm.* 161:1056–1063 (1989)). To enhance bacterial expression, the aforementioned methods can be used in conjunction with other procedures to change the plant codons in DNA constructs encoding the peptides to ones preferentially used in *E. coli.*

Using the structural information now available, it is possible to design Cyn d I peptides which, when administered to a Bermuda grass pollen sensitive individual in sufficient quantities, will modify the individual's allergic response to Bermuda grass pollen. This can be done, for example, by examining the structure of Cyn d I and producing peptides (via an expression system or synthetically) to be examined for their ability to influence B cell and/or T cell responses in Bermuda grass pollen sensitive individuals and selecting appropriate B or T cell epitopes recognized by the cells. Protein, peptides or antibodies of the present invention can also be used for detecting and diagnosing sensitivity to Bermuda grass pollen allergens. For example, this could be done by combining blood or blood products obtained from an individual to be assessed for sensitivity to Bermuda grass pollen with an isolated antigenic fragment of Cyn d I, or isolated Cyn d I, under conditions appropriate for binding of components (e.g., antibodies, T cells, B cells) in the blood with the fragment(s) or protein and determining the extent to which such binding occurs.

It is now also possible to design an agent or a drug capable of blocking or inhibiting the ability of Cyn d I to induce an allergic reaction in Bermuda grass pollen sensitive individuals. Such agents could be designed, for example, in such a manner that they would bind to relevant anti-Cyn d I-IgE's, thus preventing IgE-allergen binding and subsequent mast cell degranulation. Alternatively, such agents could bind to cellular components of the immune system, resulting in suppression or desensitization of the allergic response to Bermuda grass pollen. A non-restrictive example of this is the use of appropriate B and T cell epitope peptides, or modifications thereof, based on the cDNA/protein structures of the present invention to suppress the allergic response to Bermuda grass pollen. This can be carried out by defining the structures of B and T cell epitope peptides which affect B and T cell function in in vitro studies with blood components from Bermuda grass pollen sensitive individuals.

The DNA used in any embodiment of this invention can be cDNA obtained as described herein, or alternatively, can be any oligodeoxynucleotide sequence having all or a portion of a sequence represented herein, or their functional equivalents. Such oligodeoxynucleotide sequences can be produced chemically or mechanically, using known techniques. A functional equivalent of an oligonucleotide sequence is one which is capable of hybridizing to a complementary oligonucleotide to which the sequence (or corresponding sequence portions) thereof hybridizes, or the sequence (or corresponding sequence portion) complementary to the nucleic acid sequences, and/or which encodes a product (e.g., a polypeptide or peptide) having the same functional characteristics of the product encoded by the sequence (or corresponding sequence portion). Whether a functional equivalent must meet one or both criteria will depend on its use (e.g., if it is to be used only as an oligoprobe, it need meet only the first criterion and if it is to be used to produce Cyn d I, it need only meet the second criterion).

This invention is further illustrated by the following non-limiting examples.

EXAMPLE 1

Isolation of Cyn d I for Protein Sequencing and MAb Production

Preparation of pollen extract

Bermuda grass pollen was purchased from Greer Laboratories, Lenoir, N.C., USA. To prepare the pollen extract of soluble proteins which was loaded on the Rotofor, 5 grams of Bermuda grass pollen was extracted three times by shaking with 10 ml of 10 mM phosphate buffered saline (PBS) for one hour at 4° C. After each extraction, the mixture was centrifuged (2500 rpm, 10 minutes) and the supernatant collected. After three extractions the supernatants were pooled and filtered through a 3 mm Whatman filter.

Preparative isoelectric focusing (IEF)

Preparative IEF in the Rotofor (Biorad, Richmond, Calif.) has been described in detail by Egan et al. (1988) *Analyt. Biochem.,* 172, 488–494. Briefly, 5 ml of ampholyte solution (Bio-lyte, pH range 3–10; 40%) was added to the pollen extract and the volume adjusted to 50 ml with distilled water. This mixture was loaded into the Rotofor cell and focussed at 4° C. and 12 W constant power. After four hours, 20 fractions were collected and their pH determined. Fractions containing the proteins of interest were identified with MAb 3.2 on immunoblots after SDS-PAGE. This MAb was raised against purified Lol p I but was found to be cross-reactive with Group I homologues from nine other grasses including Bermuda grass (Kahn and Marsh, 1986, *Mol. Immunol.*, 23, 1281–1288). Fractions containing the proteins of interest were pooled and refractionated in the Rotofor using the same conditions as above except that samples were focussed for 2.5 hours. The pH of each fraction was determined.
SDS-PAGE and Western blotting Proteins in Rotofor fractions were separated under reducing conditions by electrophoresis on 10–15% gradient SDS-polyacrylamide gels. Conditions for electrophoresis were essentially as described by Singh and Knox, *Int. Archs Appl. Immun.*, 78, 300–304 (1985). Molecular weights (MW) were determined using low MW standards from Pharmacia. Proteins on polyacrylamide gels were visualized by staining with Coomassie Brilliant Blue R250.

Proteins were transferred to nitrocellulose (Schleicher and Schuell, 0.45 mm) according to Towbin et al. (1979); *Proc. Natl. Acad. Sci. U.S.A.*, 76, 4350–4354; at 120 mA overnight at 4° C. After protein transfer, non-specific binding sites were blocked by incubation of the Western blots in powdered milk [10% in 10 mM TBS (Tris-buffered saline: 150 mM NaCl/10 mM Tris.HCl, pH 7.5)].

Figure 11B:
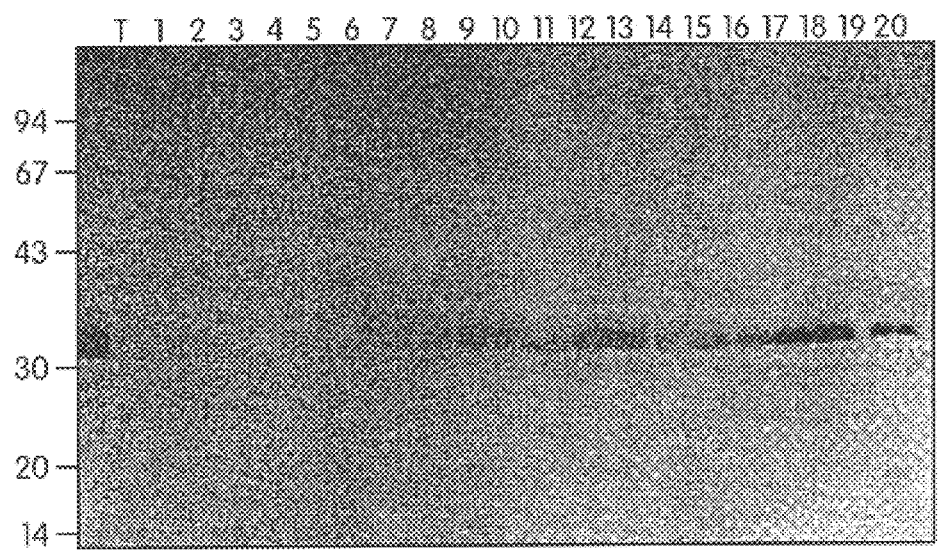
FIG. 11*b* shows a Western blot of separated proteins screened with MAb3.2.

Separation by SDS-PAGE of fractions obtained by preparative IEF, revealed that Cyn d I focussed in fractions 10–20 with a pH range of 6–10. These fractions contained 31–32 kD proteins which bound MAb 3.2. The proteins in fractions 10–13 (32 kD) which bound MAb 3.2 had a slightly higher MW than those in fractions 15–20 (3 1 kD) (FIG. 11a–b). The intermediate fraction 14 contained both proteins that bound MAb 3.2. These proteins have been designated Cyn d Ia (32 kD) (SEQ ID NO: 25) and Cyn d Ib (31 kD) (SEQ ID NOs: 26 AND 27).

Figure 12A:
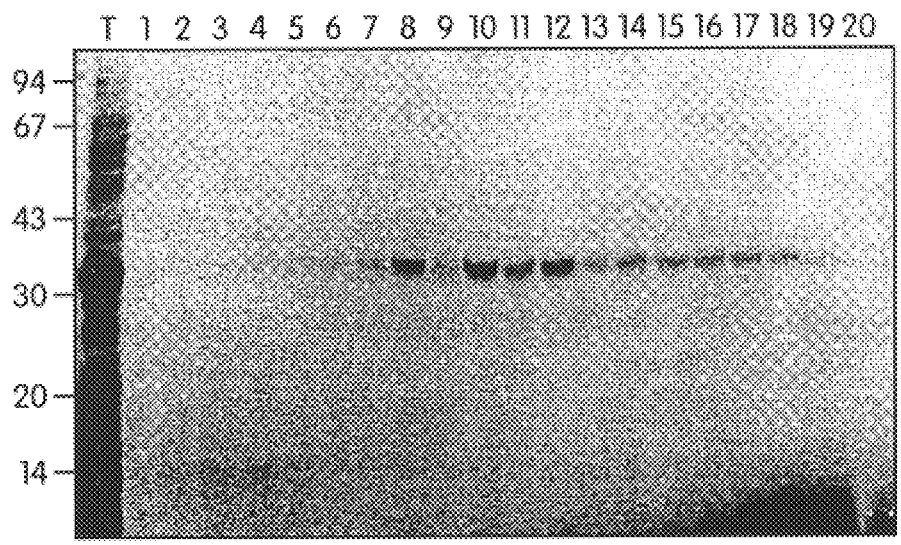
FIG. 12*a* shows a separation by SDS-PAGE of protein fractions obtained by refractionation on the Rotofor of pooled fractions, 10–13, from a primary separation of crude pollen extract.

Fractions 10–13 of FIG. 11a containing Cyn d Ia were pooled and refractionated. Cyn d Ia was found in all fractions of FIG. 12a, but dominated the protein component of fractions 13–20 (FIG. 12a). These fractions had a pH of 6.5; an indication of the pI of Cyn d Ia.

Figure 12B:
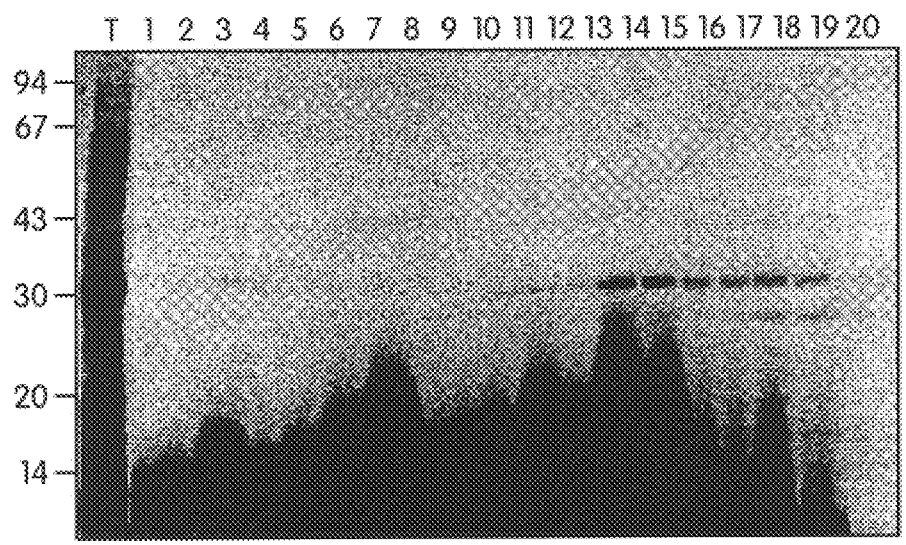
FIG. 12*b* shows separation by SDS-PAGE of protein fractions obtained by refractionation on the Rotofor of pooled fractions, 15–20, from a primary separation of crude pollen extract.

Fractions 15–20 of FIG. 11a were pooled and refractionated in order to purify Cyn d Ib. Cyn d Ib was found in all fractions of FIG. 12b but dominated the protein profile of fractions 1–12 (FIG. 12b). These fractions had a pH of 7.4; an indication of the pI of Cyn d Ib.

Immunoblot analysis

Figure 13:
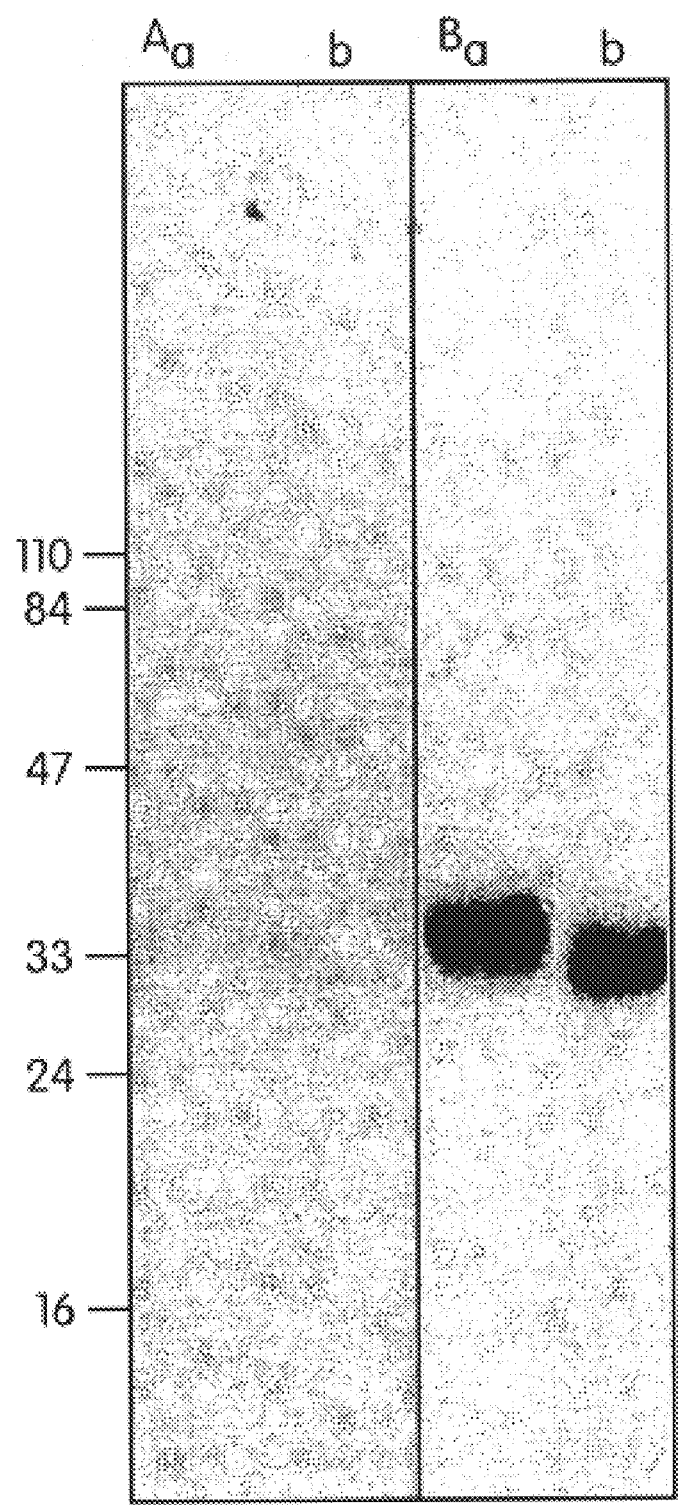
FIG. 13 shows Western blots of native Cyn d Ia and Cyn d Ib separated by SDS-PAGE and probed with IgE from sera of individuals allergic to Bermuda grass.
Figure 14A:
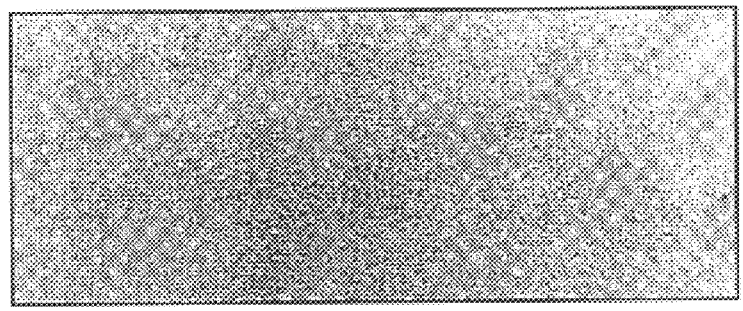
FIG. 14 shows binding of MAbs 1D1, 3A2, 3C2 and 4D2 to cDNA clones from a Cyn d I lgtII library. The number on the overlay corresponds to the cDNA clone number.
Figure 14B:
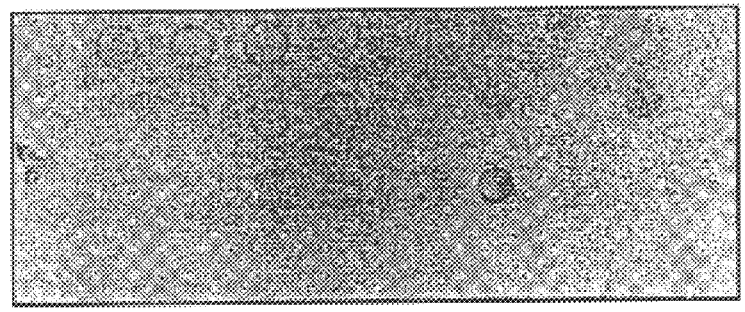
Figure 14C:
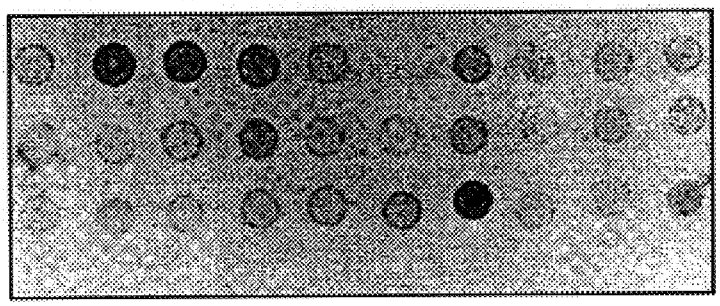
Figure 14D:
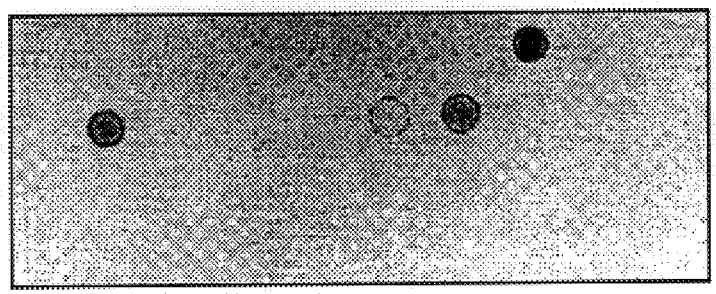

Western blots were incubated in MAb 3.2 or in sera of allergic individuals. MAb 3.2 was diluted 1:1000 in PBS containing 0.5% BSA. MAb binding was visualized by incubation in a solution of peroxidase-labelled, anti-mouse Ig antibody (Dakopatts Corporation, Carpinteria, Calif., USA) followed by addition of the enzyme substrate as described by Singh and Knox (1985) supra. Human serum was diluted 1:4 in 150 mM PBS containing 0.5% BSA. IgE binding was visualized by incubation of the blot in $^{125}$I-labelled anti-human IgE (Kallestad) (diluted 1:6 in PBS/BSA) followed by autoradiography. Purified Cyn d Ia and Ib were assessed for their ability to bind to IgE from the serum of allergic individuals (FIG. 13). Both fractions bound IgE from the sera of a Bermuda grass allergic individual.

NH$_2$-terminal amino acid sequencing

Cyn d I proteins Cyn d Ia and Cyn d Ib, isolated, as described above, and electrotransfered onto polyvinylidene difluoride (PVDF) membrane (Millipore, Bedford, Mass., USA) using 10 mM CAPS 10% methanol (pH 11.0) as the transfer buffer (Ward et al., 1990) (3 [cyclohexylamino]-1-propane sulfonic acid), were then visualized by staining with Coomassie Brilliant Blue R250, destained in methanol acetic acid water (50:10:40, v/v/v) and washed extensively with deionized water. The NH$_2$-terminal amino acid sequence of both Cyn d Ia (SEQ ID NO:25) and Cyn d Ib proteins (SEQ ID NOs: 26 and 27) was determined as described by Ward et al. (1990); Cyn d I proteins, isolated by Rotofor, were also purified using reverse-phase HPLC and the NH$_2$-terminal amino acid sequence of the 31 kD protein determined.

The two Cyn d I components show minor amino acid sequence variations in their NH$_2$-terminal regions and there is homology between Cyn d I and Lol p I from ryegrass (Table 1).

TABLE 1

NH$_2$-terminal sequences of Cyn dI isoallergens and Lol pI.

| Allergen | NH2-terminal amino-acid sequence |
|---|---|
| Cyn dIa | AMG (D) KPGPXITATYGD(K)XL(D)A(K)(T)AF(D) (SEQIDNO:25) |
| Cyn dIb+ | AIGXKPGPXITAXY(G)X(K)XLXA (SEQIDNO:26) (D) (W) (T) |
| Cyn dIb* | AIGDKPGPXITATYXXKW LDAKATFYGS NP(R) GAA (SEQIDNO:27) |
| Cyn dI$^1$ | AMGDKPGPXITATYGDKWLDAKAT FYG (SEQIDNO:47) |
| Cyn dIa/b$^2$ | AIGDKPGPXITATYGSKXLEAKATFY (SEQIDNO:48) |
| Cyn dIc$^2$ | AMGDKPGPXITAVY (SEQIDNO:49) |
| Lol pI$^3$ | IAKVPPGPNITAEYGDKWLDAKSTWYGKPT (SEQIDNO:44) |

+determined after transfer to PVDF membrane;
*determined after HPLC purification Production and screening of MAbs Anti-Cyn d I MAbs were obtained by intraperitoneal immunization of a Balb/c mouse with 50 mg of Cyn d I (isolated on the Rotofor, Biorad, Richmond, Calif.). RIBI (RIBI Immunochem, Hamilton, Mont., USA) was used as an adjuvant in the first of four immunizations. The remaining intraperitoneal immunizations were in saline. Fusion and growth of hybridomas was essentially as described by Harlow and Lane 1988, *Antibodies: A Laboratory Manual*, Cold Spring Harbor Laboratory. Single cell cloning was by limited dilution. Hybridomas producing anti-Cyn d I antibodies were identified using an ELISA assay. ELISA plates were coated overnight with 60 mg of Bermuda grass pollen extract diluted in CAPS buffer (6.67 mM NaCO$_3$ 35 mM NaHCO$_3$ pH 9.6). The wells were then washed three times with TPBS (PBS containing 0.1% Tween 20) and blocked for 30 minutes with PBS containing 1% BSA (PBS/BSA). 100 mL of primary antibody was added to each well and incubated for 60 minutes, followed by washing (as above) and incubation in b-gal labelled anti-mouse Ig (1/250 dilution in PBS/BSA, 60 minutes). After washing 200 mL of the fluorescent substrate 4-methylumbelliferyl-B-D-galactoside (MUG) was added to each well and incubated at 37° C. for 30 minutes. The plates were then read on the fluoroCount 96 flurometer (Pharmacia).

Antibodies which were positive by this method were designated 3A2, 4D2, 1D1 and 3C2 and tested for binding to Cyn d I on a Western blot of Bermuda grass pollen proteins separated by SDS-PAGE.

cDNA library and immunological screening

Poly (A+) mRNA was isolated from Bermuda grass pollen purchased from Greer Laboratories, Lenoir, N.C., USA essentially as described by Herrin and Michaels (1984). cDNA was synthesized using the Pharmacia cDNA synthesis kit and cloned into the Eco R I site of the vector lambda-gt 11. Recombinant proteins from phage plaques were transferred to nitrocellulose filters by overlaying the plated cDNA library with nitrocellulose filters impregnated with IPTG. These filters were then incubated in mixed anti-Cyn d I MAbs. Binding of MAbs to recombinant proteins was visualized as described above. Plaques producing proteins which bound to anti-Cyn d I MAbs were isolated and purified.

Isolation of cDNA clones

The Bermuda grass pollen cDNA library, as described above, was initially screened with a mixture of anti-Cyn d I hybridoma supernatants containing mainly MAb 3.2 and 30 positive cDNA clones were plaque purified. These clones were then tested for binding to anti-Cyn d I MAbs 3A2, 4D2, 3C2 and 1D1. All clones selected after the first round of screening produced recombinant fusion proteins specific for MAb 3A2. Binding of the clones to MAbs is shown in FIG. 14 and is summarized in Table 2. It is concluded that the cDNA clones isolated here encode Cyn d I based on the MAb binding shown to the recombinant fusion proteins. MAb 1D1 had a much higher background binding than the other MAbs, making its binding much more subjective.

TABLE 2

| | Monoclonal Antibody Binding | | | | |
|---|---|---|---|---|---|
| Clone | 3A2 | 4D2 | 3C2 | 1D1 | Size (bp) |
| 1 | + | | | | |
| 2 | + | | + | + | 700 |
| 3 | + | | + | + | 650 |
| 4 | + | | + | + | 500 |
| 5 | + | | | | |
| 7 | + | | + | + | |
| 8 | + | + | + | + | |
| 13 | + | | | | |
| 15 | + | | | | |
| 16 | + | | | | |
| 18 | + | + | | | 800 |
| 19 | + | | | | |
| 20 | + | | | | |
| 21 | + | | | | 400 |
| 22 | + | + | | | 800 |
| 23 | + | + | + | + | 900 |
| 24 | + | | | | |
| 25 | + | | + | | |
| 26 | + | | | | |
| 27 | + | | | | |
| 28 | + | | | | |
| 29 | + | | | | |
| 31 | + | | | | |
| 32 | + | | | | |
| 33 | + | | | | 400 |
| 34 | + | | + | + | |
| 35 | + | | | | |
| 36 | + | | | | |

Nucleotide and amino acid sequences of cDNA clones

Clones 2, 3, 18, 21, 22, 23 and 33 (see Table 2) were chosen for further study on the basis of their antibody affinity. cDNA inserts from clones 2, 3, 18, 21, 22, 23 and 33 were isolated from the phage and subcloned into pGEM-4Z (Promega) or Bluescript (Stratagene) vectors. DNA sequence was determined by double stranded sequencing carried out by the chain termination method (Sanger et al., Proc. Nat'l Acad. Sci., (1977), 74:5460–5463) using T7 polymerase (Pharmacia). The nucleotide 5 and deduced amino acid sequences of these clones are shown in FIG. 1 (clone 2) (SEQ ID NOs: 1 and 2), FIG. 2 (clone 18) (SEQ ID NOs: 3 and 4), FIG. 15 (clone 3) (SEQ ID NOs: 17 and 7), FIG. 16 (clone 22) (SEQ ID NOs: 18 and 5) and FIG. 17 (clone 23) (SEQ ID NOs: 19 and 5).

All clones sequenced show homology with each other, particularly in the open reading frame (ORF). In addition, there is significant nucleotide sequence homology between all clones sequenced and Lol p I, a major allergen of ryegrass. However, the sequenced clones can be separated into three groups on the basis of nucleotide and deduced amino acid sequence homology, those with sequence most similar to clone 2 (i.e., clone 3), those with sequence most similar to clone 18 (i.e., clones 21 and 33), and those most similar to clone 22 (i.e., clone 23). The deduced amino acid sequences encoded by the ORFs of clones 18 (SEQ ID NOs: 4) and 2 (SEQ ID NO: 2) were compared to the deduced amino acid sequence of Lol p I (Perez et al, 1991 supra; Griffith et al, 1991, supra) (FIG. 6). There is 67% amino acid homology between Lol p I and clone 18 and 72% between Lol p I and clone 2. The deduced amino acid sequences of clones 2 (SEQ ID NO: 2) and 18 (SEQ ID NO: 4) have 83% identity (87% homology) with each other.

EXAMPLE 2

Cloning the 5' End of Cyn d I

Double-stranded cDNA was synthesized from approximately 4 mg of pollen RNA (Greer Labs, Lenoir, N.C., USA) using the cDNA Synthesis System Plus kit (BRL, Bethesda, Md., USA). After a phenol extraction and ethanol precipitation, the cDNA was blunted with T4 DNA polymerase (Promega, Madison, Wis., USA), and ligated to ethanol precipitated, self-annealed, AT, 5'-GGGTCTAGAGGTACCGTCCGATC-GATCATT-3', and AL, 5'-p-AATGATCGATGCT-3' (SEQ ID NO: 29), oligonucleotides for use in a modified Anchored PCR (Marsh et al, 1986: Roux and Dhanarajan, 1990; Rafnar et al, 1991) reaction. cDNA encoding the amino terminus of Cyn d I was amplified from the linkered cDNA (5 ml from a 20 ml reaction) with I mg each of oligonucleotides AP, 5'-GGGTCTAGAGGTACCGTCCG-3' (SEQ ID NO: 30), and CD-5, 5'-GATGTGCTCGTAGTTCTT-3' (SEQ ID NO: 31), an oligonucleotide primer based on non-coding strand sequence of Cyn d I corresponding to the amino acid sequence KNYEHI (SEQ ID NO: 32). The primary polymerase chain reactions (PCR) were carried out in a programmable thermal controller from MJ Research, Inc. (Cambridge, Mass., USA) using the GeneAmp DNA Amplification kit (Perkin Elmer Cetus, Norwalk, Conn., USA) in a reaction containing 10 ml 10× buffer containing dNTPs, 1 mg of each primer, cDNA, 0.5 ml Amplitaq DNA polymerase, and distilled water to 100 ml. Twenty-five rounds of amplification consisted of denaturation at 94° C. for 1 minute, annealing of primers to the template at 65° C. for 1.5 minutes, and chain elongation at 72° C. for 2 minutes. Five percent (5 ml) of this primary amplification was then used in a secondary amplification with 1 mg each of CD-4, 5'-GGGGATCCGAGGCCGT-CCTTGAAG-3' (SEQ ID NO: 33), a Cyn d I oligonucleotide primer nested relative to CD-5 (SEQ ID NO: 31) based on non-coding strand sequence corresponding to amino acids IFKDGL (SEQ ID NO: 34), and AP (SEQ ID NO: 30), as above. All oligonucleotides were synthesized by Research Genetics, Inc (Huntsville, Ala.). Oligonucleotide primers AP (SEQ ID NO: 30), AT (SEQ ID NO: 28) and AL (SEQ ID NO: 29) have been previously described (Rafnar et al, 1991; Morgenstern et al, 1991; Griffith et al, 1991; Rogers et al, 1991). The first eight nucleotides of CD-4 (SEQ ID NO: 33) were added to create a Bam HI restriction site for cloning purposes.

Amplified DNA was recovered by sequential chloroform, phenol, and chloroform extractions, followed by precipitation at −20° C. with 0.5 volumes of 7.5 ammonium acetate and 1.5 Volumes of isopropanol. After precipitation and washing with 70% ethanol, the DNA was simultaneously digested with Xba I and Bam HI in a 15 ml reaction and electrophoresed through a preparative 3% SeaPlaque low melt agarose gel (FMC Corp., Rockland Me., USA). The appropriate sized DNA band was visualized by ethidium bromide (EtBr) staining, excised, and ligated into appropriately digested M13mp19 for dideoxy DNA sequencing (Sanger et al, (1977), *Proc. Nat'l. Acad. Sci USA*, 74:5460–5463) with the Sequenase kit (U.S. Biochemicals, Cleveland, Ohio, USA). Two clones, 14a1 (SEQ ID NO: 10) and 14c1 ID NO: 12), were obtained from this ligation, completely sequenced and found to contain in-frame initiator methionines. The methionine encoded by nucleotides 28–30 of the 14a1 sequence (SEQ ID NO: 12) (FIG. 6) most preferably represents the initiating codon since the surrounding sequence closely matches the common plant sequence, 5'-AACAATGGC-3' (SEQ ID NO: 46) (Lutcke at al, (1987) *Embo. J.,* 6:43–48), and there is an in-frame stop codon just upstream. Although 14c1 (SEQ ID NO: 12) (FIG. 7) contained two potential in-frame methionines, the methionine encoded by nucleotides 27–29 is most probably the initiator methionine since the surrounding sequence more closely matches the consensus plant sequence, 5'-AACAATGGC-3' (SEQ ID NO: 46) (Lutcke at al, supra), than does the methionine encoded by nucleotides 42–45 (78% vs. 56% match). Furthermore, the sequence surrounding nucleotides 27–29 is identical to that of clone 14a1 (SEQ ID NO: 10). Both clone 14a1 (SEQ ID NO: 10) and clone 14c1 (SEQ ID NO: 12) sequences had 17 nucleotide overlaps with the longest Cyn d I clone, clone 18 (SEQ ID NO: 3). The amino terminus of the mature Cyn d I $NH_2$-AIGDKPGPNITATGNKWLEAKATFYG (SEQ ID NO: 35) encoded by clone 14a1 and $NH^2$-AIGDKPGPNITATGSKWLEAKATFYG-(SEQ ID NO: 36) encoded by clone 14c1 could be identified by comparison with two previously published protein sequences for Cyn d I: NH2-AMGDKPGP?ITATYGDKWLDAKATFYG (SEQ ID NO: 41) (Matthiesen et al, 1988, supra; Matthiesen et al, 1990, supra; Matthiesen et al, 1991, supra) and NH2-AIGDKPGPKITATY??KWLEAKAT (SEQ ID NO: 45) (Singh et al, 1990, supra). This indicated that clones 14a1 and 14c1 had leader sequences of 22 and 26 amino acids, respectively. These leader sequences would be cleaved to create the mature form of the Cyn d I protein. The potential full-length amino acid sequence of Cyn d I designated Cyn d I.18 (SEQ ID NO: 15) (FIG. 9) was created by attaching the sequence of Cyn d I.14 (SEQ ID NO: 14) to clone 18 (SEQ ID NO: 4) at their overlap as shown in FIG. 9. In both cases, the mature form of Cyn d I is predicted to be 246 amino acids with a calculated molecular weight of 26.7 kDa.

EXAMPLE 3

RNA was isolated from the pollen of *Cynodon dactylon* using a modification of the guanidinium thiocyanate method of Chomczynski and Sacchi (1987) *Analytical Biochem.* 162: 156–159. Pollen was ground in liquid nitrogen with 9 mls of guanidinium thiocyanate buffer (5M guanidinium thiocyanate in 0.05% Tris-HCl [pH 7.0], 0.05 vol. β-mercaptoethanol, 0.1 vol. 5% sodium lauroyl sarkosine). The pollen solution was then shaken with phenol (10 ml) for 10 min, after which 10 ml of chloroform:isoamyl alcohol 24:1 was added and the mixture shaken for a further 20 min. The mixture was centrifuged at 7,000×g for 25 min and the aqueous phase collected.

The aqueous phase was re-extracted with phenol:chloroform:isoamyl alcohol 25:24:1 followed by centrifugation at 2,000×g until the interface was clear. The aqueous phase was then decanted into a quickseal ultracentrifuge tube, underlain with a 3 ml CsCl cushion (5.7 M CsCl in 0.1 M EDTA; density=1.71 g/ml) and centrifuged (20 hrs, 40,000 rpm, 20° C.) in a Beckman Ti 70.1 rotor (Beckman L8-70 ultracentrifuge; Beckman Instruments, Fullerton, Calif.). After centrifugation, RNA in the pellet was resuspended in 0.05% SDS, phenol/chloroform extracted and ethanol precipitated overnight at −20° C.

Poly $A^+$ RNA was isolated using a Pharmacia mRNA Purification kit (Pharmacia, Piscataway, N.J.), following the manufacturers instructions.

First strand cDNA was prepared by heating 0.8 μg mRNA to 70° C. with 0.5 μg of oligo-dT primer (Pharmacia, Piscataway, N.J.). After the mRNA solution was cooled on ice, 5× first strand buffer and 25U RNAsin ribonuclease inhibitor were added. The mixture was then heated at 42° C. for 1 hr. Final reaction conditions were 50 mM Tris-HCl, pH 8.3, 50 mM KCl, 10 mM $MgCl_2$, 0.5 mM spermidine, 10 mM DTT, 4 mM sodium pyrophosphate, 1 mM each of dATP, dCTP, dGTP, and TTP, 25U RNAsin ribonuclease inhibitor and 15 u AMV reverse transcriptase/μg RNA (Promega cDNA synthesis kit, Promega, Madison, Wis.) in a final volume of 25 μl. cDNA sequences encoding Cyn d I were amplified using the Perkin-Elmer Cetus gene amplification kit (U.S. Biochemicals, Cleveland, OH). 5 μl (25%) of the first strand cDNA synthesis product was mixed with 10× buffer to a final buffer concentration of 2 mM $MgCl_2$, 50 mM KCl, 10 mM Tris-HCl, 1 μg of oligonucleotide primer CDI5N, 5'-GGGAATTCGCCATCGGCG-ACAAG-CCAG-3' (SEQ ID NO: 37), 1 μg of oligonucleotide primer CD13'B18, 5'-CCCTGCAGATG-GAGGATCATCGTCTC-3' (SEQ ID NO: 38), 0.2 mM dNTP and 2.5 units of Taq DNA polymerase (Pharmacia, Piscataway, N.J.). Nucleotides 1–8 of CDI5'N (SEQ ID NO: 37) were added to create an Eco RI endonuclease restriction site for cloning purposes, while nucleotides 9–27 correspond to nucleotides 107 to 125 of clone 14a1 (SEQ ID NO: 10) in FIG. 6 that encode amino acids 1–6 (AIGDKP) (SEQ ID NO: 50) of Cyn d I (Table I, FIGS. 8 and 9). Nucleotides 1–8 of CDI3'B18 (SEQ ID NO: 38) were added to create a Pst I endonuclease restriction site for cloning purposes, while nucleotides 9–26 correspond to non-coding strand sequence complementary to nucleotides 604 to 621 of clone 18 (SEQ ID NO: 3) (FIG. 2).

The PCR was performed in a Perkin-Elmer Cetus Thermal Cycler (Perkin-Elmer, Norwalk, Conn.) and consisted of 5 cycles of denaturation (94° C., 1 min), annealing (45° C., 1.5 min), and elongation (72° C., 3 min) followed by 20 cycles of denaturation (94° C., 1 min), annealing (55° C., 1.5 min), and elongation (72° C., 3 min). The final elongation reaction was performed at 72° C. for 10 min. Amplified product was recovered by phenol extraction, chloroform extraction, and then precipitation at −20° C. with 0.5 vol 7.5 M ammonium acetate and 1.5 volumes isopropanol. Reaction product was blunted with Klenow fragment of DNA polymerase then cut with Eco RI and cloned into Bluescript vector digested with Eco RI and Hin cII. The clone CD1 was sequenced by the dideoxy chain termination method (Sanger, supra), as described in Example 1, and found to contain the nucleotide and deduced amino acid sequences of Cyn d I shown in FIG. 18 (SEQ ID NOs: 20 and 21).

EXAMPLE 4

Double stranded cDNA was prepared and amplified using oligonucleotide primers CD-13 (SEQ ID NO: 39) and CD-15 (SEQ ID NO: 40) in a primary PCR reaction as described in Example 2. CD-13 has the sequence 5'-TTTCTAGAGCCATCGGCGACAAGCCAGGG-CCC-3' (SEQ ID NO: 39), whereas nucleotoide 14 could be C or G. Nucleotides 1 through 8 of CD-13 (SEQ ID NO: 39)

(5'-TTTCTAGA-3') were added to create a Xba I restriction site for cloning purposes. The remaining nucleotides encoded amino acids Ala(Ile/Met)GlyAspLysProGlyPro, where amino acid 2 could be either Ile or Met (amino acids I through 8 of Cyn d Ia (SEQ ID NO: 25) and Cyn d Ib (SEQ ID NO: 27) (Table I). CD-15 has the sequence 5'-GCGTACTTCACGAGCAGCGCCAG-GTAATT-3' (SEQ ID NO: 40), which corresponds to non-coding strand sequence complementary to coding strand sequence that encodes amino acids AsnTyrLeuAlaLeuLeuValLysTyrAla (numbered amino acids 159 through 168 of clone 2 (C2) (SEQ ID NO: 2) and clone 3 (SEQ ID NO: 7) (C3) in FIG. 5). Five percent of the primary reaction was amplified in a secondary PCR, as described in Example 2, using oligonucleotide primers CD-13 (SEQ ID NO: 39) and CD-16. CD-16 has the sequence 5'-TTGAATTCGACACGGCGGAACTGCAGCAT-3' (SEQ ID NO: 6), where nucleotide 12 could be G or A. Nucleotides 1 through 8 of CD-16 (SEQ ID NO: 6) were added to create an Eco RI restriction site for cloning purposes. Nucleotides 9 through 29 corresponded to non-coding strand sequence complementary to coding strand sequence that encode amino acids MetLeuGlnPheArgArgVal (numbered amino acids 132 through 138 of C2 (SEQ ID NO: 2) and C3 (SEQ ID NO: 7) in FIG. 5).

The PCR amplifications were performed as described in Example 2. Amplified product was recovered, appropriately digested and ligated into pUC for sequencing as described in Example 2. A clone, designated KAT-39-1, was isolated that had sequence identifying it as a Cyn d I clone. The nucleotide and deduced amino acid sequences of clone KAT-39-1 are shown in FIG. 19 (SEQ ID NO: 22 and 2. This clone is an extension of the Cyn d I clones C2 (SEQ ID NO: 1) and C3 (SEQ ID NO: 17). Oligonucleotides CD-15 (SEQ ID NO: 40) and CD-16 (SEQ ID NO: 6) have single nucleotide mismatches at their 3' ends with the corresponding sequence in Cyn d I clone C18 (SEQ ID NO: 3) and its homologues. Therefore, only clone C2 or C3, or a close family member would be amplified. A composite sequence of KAT-39-1 (SEQ ID NO: 23) and Cyn d I.2/3 (SEQ ID NO: 16) designated Cyn d I.2/3 (full-length) (SEQ ID NO: 24), is shown in FIG. 20 in comparison to Cyn d I.CD1 (SEQ ID NO: 21) and Cyn d I.18 (SEQ ID NO: 15).

Although the invention has been described with reference to its preferred embodiments, other embodiments can achieve the same results. Variation and modifications to the present invention will be obvious to those skilled in the art and it is intended to cover in the appended claims all such modifications and equivalents that follow in the true spirit and scope of this invention.

What is claimed is:

1. An isolated Cyn dI protein allergen comprising an amino acid sequence selected from the group consisting of Cyn dI.18 (SEQ ID NO: 15), Cyn dI.CD1 (SEQ ID NO: 21) and Cyn dI 2/3 (SEQ ID NO: 24), all as shown in FIG. 20.

2. An isolated Cyn dI protein allergen which is encoded by a nucleic acid sequence having the formula:

$$L_1 NYX$$

wherein $L_1$ is a nucleic acid sequence of 0–300 nucleotides which nucleic acid sequence includes nucleotides encoding a leader sequence of Cyn dI, N is a nucleic acid sequence comprising up to 600 nucleotides which nucleic acid contains nucleotides encoding the amino terminus portion of mature Cyn dI, Y is the portion of the nucleic acid sequence of clone 2 (SEQ ID NO: 1), clone 18 (SEQ ID NO: 3), clone 3 (SEQ ID NO: 17), clone 22 (SEQ ID NO: 18), clone 23 (SEQ ID NO: 19) or any polymorphic form thereof that codes for mature Cyn dI, and X is nucleic acid sequence of 0–600 nucleotides which nucleic acid sequence includes nucleotides of the 3' untranslated portion of Cyn dI, and wherein the nucleic acid sequence of N does not overlap the 5' end of the nucleic acid sequence of Y and wherein $L_1$ and X can be 0, and wherein the isolated Cyn dI protein allergen is free of all other Bermuda grass pollen protein allergens.

3. A therapeutic composition comprising the Cyn dI protein allergen of claim 1 or 2, and a pharmaceutically acceptable carrier or diluent.

* * * * *